United States Patent
Herz et al.

(10) Patent No.: US 10,149,836 B2
(45) Date of Patent: Dec. 11, 2018

(54) ISOXAZOLE TREATMENTS FOR FRONTOTEMPORAL DEMENTIA

(71) Applicant: The Board of Regents of the University of Texas System, Austin, TX (US)

(72) Inventors: Joachim Herz, Dallas, TX (US); Gang Yu, Dallas, TX (US); Bruce Posner, Dallas, TX (US); Basar Cenik, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/127,603

(22) PCT Filed: Mar. 20, 2015

(86) PCT No.: PCT/US2015/021717
§ 371 (c)(1),
(2) Date: Sep. 20, 2016

(87) PCT Pub. No.: WO2015/143300
PCT Pub. Date: Sep. 24, 2015

(65) Prior Publication Data
US 2017/0172987 A1    Jun. 22, 2017

Related U.S. Application Data

(60) Provisional application No. 61/968,875, filed on Mar. 21, 2014.

(51) Int. Cl.
*A61K 31/422* (2006.01)
*C07D 263/56* (2006.01)
*C07D 413/14* (2006.01)
*C07D 413/04* (2006.01)
*C07D 261/18* (2006.01)
*C07D 495/04* (2006.01)
*C07D 209/40* (2006.01)
*A61K 31/404* (2006.01)
*A61K 31/42* (2006.01)
*A61K 31/423* (2006.01)
*A61K 31/454* (2006.01)
*A61K 31/5377* (2006.01)
*A61K 45/06* (2006.01)

(52) U.S. Cl.
CPC .......... *A61K 31/422* (2013.01); *A61K 31/404* (2013.01); *A61K 31/42* (2013.01); *A61K 31/423* (2013.01); *A61K 31/454* (2013.01); *A61K 31/5377* (2013.01); *A61K 45/06* (2013.01); *C07D 209/40* (2013.01); *C07D 261/18* (2013.01); *C07D 263/56* (2013.01); *C07D 413/04* (2013.01); *C07D 413/14* (2013.01); *C07D 495/04* (2013.01)

(58) Field of Classification Search
CPC .................................................... A61K 31/422
USPC ....................................................... 514/236.8
See application file for complete search history.

(56) References Cited

U.S. PATENT DOCUMENTS

| 8,193,225 | B2 | 6/2012 | Schneider et al. |
| 2007/0293538 | A1 | 12/2007 | Hobden |
| 2009/0203690 | A1 | 8/2009 | Akritopoulou-Zanze et al. |

FOREIGN PATENT DOCUMENTS

| WO | WO 2006/065204 | 6/2006 |
| WO | WO 2007/126041 | 11/2007 |
| WO | WO 2010/142801 | 12/2010 |
| WO | WO 2012/135097 | 10/2012 |
| WO | WO 2012/162249 | 11/2012 |

OTHER PUBLICATIONS

Neumann et al,. Brain (2009), vol. 132(11), pp. 2922-2931.*
Angene1, "Benzoxazole, 2,3-dihydro-2-phenyl," 2010. (Retrieved from Internet at www.angenechemical.com/productshow/AGNPC00O6EJ.html, May 19, 2015.).
Angene2, "N-prop-2-eny1-5-thiophen-2-y1-1, 2-oxazole-3-carboxamide," 2010. (Retrieved from Internet at www.angenechemical.com/productshow/AGN-PC-00R4FA.html, May 19, 2015.).
Bowen et al., "Imbalance of a serotonergic system in frontotemporal dementia: implication for pharmacotherapy," *Psychoparhmacology*, 196:603-610, 2008.
Capell et al., "Rescue of progranulin deficiency associated with frontotemporal lobar degeneration by alkalizing reagents and inhibition of vacuolar ATPase," *J. Neurosci.*, 31:1885-1894, 2011.
Cenik et al., "Suberoylanilide hydroxamic acid (vorinostat) up-regulates progranulin transcription,"*The Journal of Biological Chemistry*, 286(18):16101-16108, 2011.
Finch et al., "Plasma progranulin levels predict progranulin mutation status in frontotemporal dementia patients and asymptomatic family members," *Brain*, 132(Pt 3):583-591, 2009.
PCT International Preliminary Report on Patentability issued in International Application No. PCT/US2015/021717, dated Sep. 29, 2016.
PCT International Search Report and Written Opinion issued in International Application No. PCT/US2015/021717, dated Jul. 2, 2015.
Rosen, "CRC Project—SAHA as a potential therapeutic in GRN+ FTD," Feb. 2014. (Retrieved from Internet at www.biomath.info/protocols/medicine/docs/ezrarosen.pdf, May 19, 2015.).

(Continued)

*Primary Examiner* — Taofiq A Solola
(74) *Attorney, Agent, or Firm* — Parker Highlander PLLC

(57) ABSTRACT

The subject matter described here relates to the use of compounds and methods for the increase of progranulin expression. The methods may take place in vitro, ex vivo such as in isolates from adult mammalian tissue, or in vivo. Compounds and methods described herein may find use in the treatment of frontotemporal dementia.

18 Claims, 6 Drawing Sheets
Specification includes a Sequence Listing.

(56) References Cited

OTHER PUBLICATIONS

Sleegers et al., "Serum biomarker for progranulin-associated frontotemporal lobar degeneration," Ann. Neurol., 65:603-609, 2009.
Yin et al., "Exaggerated inflammation, impaired host defense, and neuropathology in progranulin-deficient mice," J. Exp. Med., 207(1):117-128, 2010.

* cited by examiner

ISOXAZOLE TREATMENTS FOR FRONTOTEMPORAL DEMENTIA

This application is a national phase application under 35 U.S.C. § 371 of International Application No. PCT/US2015/021717, filed Mar. 20, 2015, which claims benefit of priority to U.S. Provisional Application Serial No. 61/968,875, filed Mar. 21, 2014, the entire content of each of which is hereby incorporated by reference.

BACKGROUND

1. Field

The present disclosure relates generally to the fields of cell biology, developmental biology and medicine. More particularly, it concerns methods and compositions relating to the stimulation of progranulin expression and the treatment and prevention of frontotemporal lobar degeneration, resulting in frontotemporal dementia.

2. Description of Related Art

Frontotemporal dementia (FTD) is a clinical syndrome characterized by progressive deterioration of decision-making abilities, control of behavior, and language, with relative early sparing of memory. It is the second most frequent presenile dementia disorder, and ~25% of the cases are hereditary (van Swieten and Heutink 2008). A common pathological manifestation of FTD is frontotemporal lobar degeneration with TDP-43 inclusions. FTD is a devastating and generally fatal disease. Median survival after diagnosis is 10 years (Hodges et al. 2003). Current treatment options are limited to management of emotional and behavioral aspects with antidepressants and social interventions (Kirshner 2010).

Familial cases of FTD are frequently caused by loss-of-function mutations of the GRN gene (van Swieten and Heutink 2008; Cruts et al., 2006; Baker et al., 2006 and Gass et al., 2006). The protein encoded by this gene, progranulin (also called GRN protein, human granulin precursor, proepithelin, acrogranin, and PC cell-derived growth factor), is a secreted glycoprotein with growth factor-like and immunomodulatory activities (Ahmed et al., 2007). It was recently identified as a TNF receptor antagonist (Tang et al., 2011). Progranulin contains one half-length and seven full-length granulin domains, which are released following proteolytic cleavage. Biological effects, including promotion of neuronal survival, neurite outgrowth, and regulation of microglial inflammatory responses, have been attributed to both the full-length protein and the granulin peptides (Eriksen and Mackenzie 2008).

To date, >60 pathogenic GRN mutations have been reported in patients with FTD, and all are expected to result in haploinsufficiency. Progranulin-deficient mice display dysregulated immune responses in the brain and recapitulate phosphorylated cytoplasmic TDP-43 aggregates seen in FTD brains (Yin et al., 2010). Furthermore, the concentration of progranulin in the serum is reported to be lower in patients and mutation carriers compared with healthy controls (Sleegers et al., 2009 and Finch et al., 2009), suggesting that reduced progranulin expression causes FTD. Therefore, increasing progranulin expression from the wild-type allele may prevent or slow down disease progression.

Following this rationale, Capell et al. (Capell et al., 2011) recently reported that alkalizing drugs and vacuolar ATPase inhibitors increase progranulin protein levels through a post-transcriptional mechanism. Since this mechanism likely involves reduced turnover or lysosomal conversion to mature granulins, the value of this approach for disease prevention or treatment is doubtful. Thus, identification of additional drugs that increase progranulin expression at the most proximal, i.e., transcriptional level is essential to slow down or reverse the cognitive decline of FTD will prove extremely valuable.

SUMMARY

Thus, in accordance with the present disclosure, there is provided a method of treating a subject having or suspect of having frontotemporal dementia comprising administering to said subject an effective amount of a 3',5'-disubstituted isoxazole having the formula:

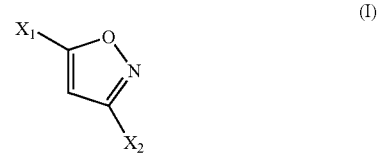

wherein $X_1$ is alkyl$_{(C\leq12)}$ or heteroaryl$_{(C\leq12)}$, or a substituted version of any of these groups; or $X_i$ is

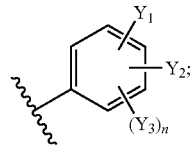

wherein $Y_1$ and $Y_2$ are each independently selected from hydrogen, halo, hydroxy, amino, nitro, or cyano, or alkyl$_{(C\leq12)}$, alkoxy$_{(C\leq12)}$, alkylamino$_{(C\leq12)}$, dialkylamino$_{(C\leq12)}$, or $Y_1$ and $Y_2$ are taken together to form

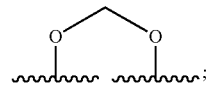

$Y_3$ is hydrogen, halo, hydroxy, amino, aminosulfonyl, nitro, cyano, mercapto, or phosphate; alkyl$_{(C\leq12)}$, alkenyl$_{(C\leq12)}$, alkynyl$_{(C\leq12)}$, aryl$_{(C\leq12)}$, heteroaryl$_{(C\leq12)}$, aralkyl$_{(C\leq12)}$, acyl$_{(C\leq12)}$, alkyloxy$_{(C\leq12)}$, alkenyloxy$_{(C\leq12)}$, alkynyloxy$_{(C\leq12)}$, aryloxy$_{(C\leq12)}$, heteroaryloxy$_{(C\leq12)}$, aralkyloxy$_{(C\leq12)}$, acyloxy$_{(C\leq12)}$, alkylamino$_{(C\leq12)}$, dialkylamino$_{(C\leq12)}$, alkenylamino$_{(C\leq12)}$, alkynylamino$_{(C\leq12)}$, arylamino$_{(C\leq12)}$, heteroarylamino$_{(C\leq12)}$, aralkylamino$_{(C\leq12)}$, amido$_{(C\leq12)}$, alkylsulfonylamino$_{(C\leq12)}$, alkylsulfonyl$_{(C\leq12)}$, arylsulfonyl$_{(C\leq12)}$, or a substituted version of these groups; n is 1, 2, or 3; and $X_2$ is aryl$_{(C<12)}$, substituted aryl$_{(C<12)}$, or —C(O)NR$_1$R$_2$; wherein R$_1$ and R$_2$ are independently selected from hydrogen, alkyl$_{(C\leq12)}$, substituted alkyl$_{(C\leq12)}$, alkenyl$_{(C\leq12)}$, substituted alkenyl$_{(C\leq12)}$, alkynyl$_{(C\leq12)}$, substituted alkynyl$_{(C\leq12)}$, aryl$_{(C\leq12)}$, substituted aryl$_{(C\leq12)}$, heteroaryl$_{(C\leq12)}$, substituted heteroaryl$_{(C\leq12)}$, aralkyl$_{(C\leq12)}$, substituted aralkyl$_{(C\leq12)}$, heteroaralkyl$_{(C\leq12)}$, substituted heteroaralkyl$_{(C\leq12)}$, or -A-Y$_4$ wherein A is alkanediyl$_{(C\leq12)}$ or substituted alkanediyl$_{(C\leq12)}$ and Y$_4$ is

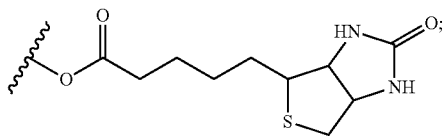 [SMILES: *OC(=O)CCCCC1SCC2NC(=O)NC21]

or when $R_1$ and $R_2$ are taken together, $R_1$ and $R_2$ are alkanediyl$_{(C\leq12)}$, alkoxydiyl$_{(C\leq12)}$, alkylaminodiyl$_{(C\leq12)}$, or a substituted version of any of these groups; or a compound of the formula:

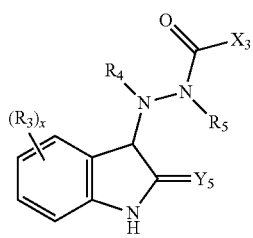

wherein:

$X_3$ is aryl$_{(C\leq12)}$, heteroaryl$_{(C\leq12)}$, or a substituted version of any of these groups; $Y_5$ is O, S, or NH; $R_3$ is amino, cyano, halo, hydroxy, nitro, hydroxysulfonyl, aminosulfonyl, alkyl$_{(C\leq8)}$, substituted alkyl$_{(C\leq8)}$, alkoxy$_{(C\leq8)}$, substituted alkoxy$_{(C\leq8)}$, acyl$_{(C\leq8)}$, substituted acyl$_{(C\leq8)}$, amido$_{(C\leq8)}$, substituted amido$_{(C\leq8)}$, alkylamino$_{(C\leq8)}$, substituted alkylamino$_{(C\leq8)}$, dialkylamino$_{(C\leq8)}$, or substituted dialkylamino$_{(C\leq8)}$; x is 0, 1, 2, 3, or 4; and $R_4$ and $R_5$ are each independently selected from hydrogen, alkyl$_{(C<6)}$, or substituted alkyl$_{(C<6)}$; or a compound of the formula:

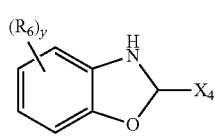

wherein: $X_4$ is aryl$_{(C\leq12)}$, aralkyl$_{(C\leq12)}$, heteroaryl$_{(C\leq12)}$, or a substituted version of any of these groups; $R_6$ is amino, cyano, halo, hydroxy, nitro, hydroxysulfonyl, aminosulfonyl, alkyl$_{(C\leq8)}$, substituted alkyl$_{(C\leq8)}$, alkoxy$_{(C\leq8)}$, substituted alkoxy$_{(C\leq8)}$, acyl$_{(C\leq8)}$, substituted acyl$_{(C\leq8)}$, amido$_{(C\leq8)}$, substituted amido$_{(C\leq8)}$, alkylamino$_{(C\leq8)}$, substituted alkylamino$_{(C\leq8)}$, dialkylamino$_{(C\leq8)}$, or substituted dialkylamino$_{(C\leq8)}$; and y is 0, 1, 2, 3, 4; or a pharmaceutically acceptable salt thereof.

In a more particular embodiment, the isoxazole may be further defined by the formula:

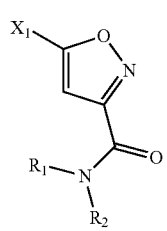

wherein $X_1$ is heteroaryl$_{(C\leq12)}$ or substituted heteroaryl$_{(C\leq12)}$; and $R_1$ and $R_2$ are independently selected from hydrogen, alkyl$_{(C\leq12)}$, substituted alkyl$_{(C\leq12)}$, alkenyl$_{(C\leq12)}$, heteroaralkyl$_{(C\leq12)}$, or -A-$Y_4$, wherein A is alkanediyl$_{(C\leq12)}$ or substituted alkanediyl$_{(C\leq12)}$ and $Y_4$ is

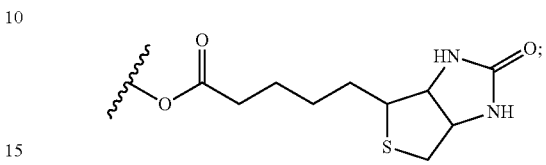

or when $R_1$ and $R_2$ are taken together, $R_1$ and $R_2$ are alkanediyl$_{(C\leq12)}$, alkoxydiyl$_{(C\leq12)}$, alkylaminodiyl$_{(C\leq12)}$, or a substituted version of any of these groups; or a salt thereof.

In other embodiments, the the compound is further defined as:

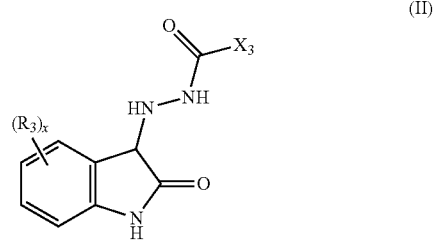

wherein: $X_3$ is aryl$_{(C\leq12)}$, heteroaryl$_{(C\leq12)}$, or a substituted version of any of these groups; $R_3$ is amino, cyano, halo, hydroxy, nitro, hydroxysulfonyl, aminosulfonyl, alkyl$_{(C\leq8)}$, substituted alkyl$_{(C\leq8)}$, alkoxy$_{(C\leq8)}$, substituted alkoxy$_{(C\leq8)}$, acyl$_{(C\leq8)}$, substituted acyl$_{(C\leq8)}$, amido$_{(C\leq8)}$, substituted amido$_{(C\leq8)}$, alkylamino$_{(C\leq8)}$, substituted alkylamino$_{(C\leq8)}$, dialkylamino$_{(C\leq8)}$, or substituted dialkylamino$_{(C\leq8)}$; and x is 0, 1, 2, 3, or 4; or a pharmaceutically acceptable salt thereof. In other embodiments, the compound is a compound of formula III.

The isoxazole may have $X_1$ selected from 2-thienyl or 3-thienyl, and/or the isoxazole may have $X_2$ of —C(O)N$R_1R_2$. The isoxazole may have $R_1$ and $R_2$ selected from alkyl$_{(C\leq12)}$ or substituted alkyl$_{(C\leq12)}$. The isoxazole may have $R_1$ and $R_2$ selected from —CH$_2$CH$_2$CH$_2$CH$_3$, —CH$_2$(CH$_2$)$_4$CH$_2$OH, —CH$_2$CH$_2$CH$_3$, —CH$_2$(CH$_2$)$_3$CH$_2$OH, cyclobutyl, or cyclopentyl. The isoxazole may have $R_1$ and $R_2$ selected from alkenyl$_{(C\leq12)}$ or heteroaralkyl$_{(C\leq12)}$. The isoxazole may have $R_1$ and $R_2$ of —CH$_2$CHCH$_2$. The isoxazole may have $R_1$ and $R_2$ taken together as alkanediyl$_{(C\leq12)}$, alkoxydiyl$_{(C\leq12)}$, or a substituted version of either of these groups. The isoxazole may further be defined as a formula selected from:

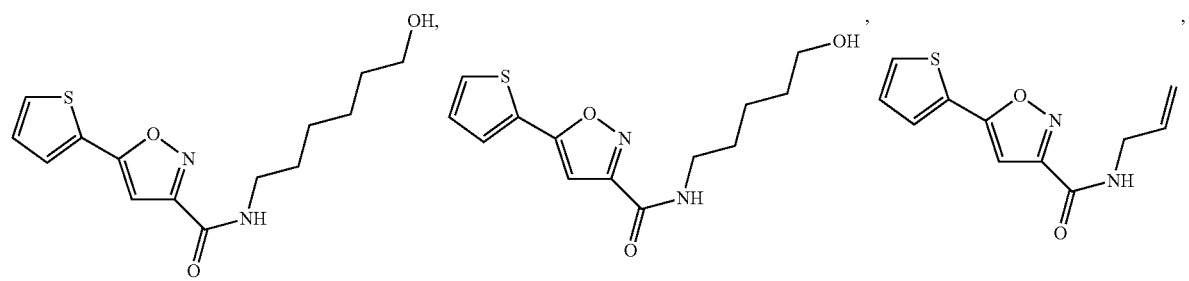
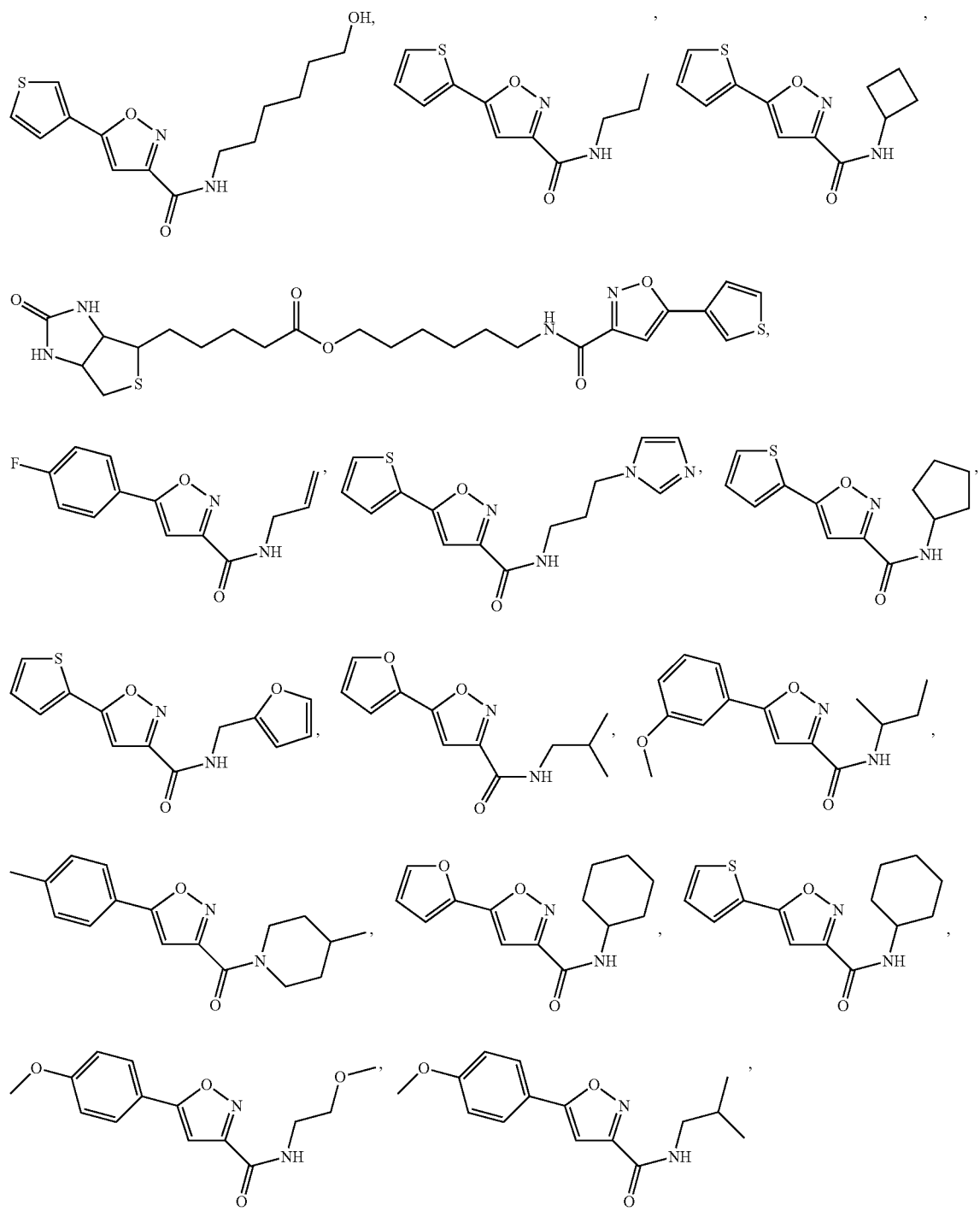

-continued

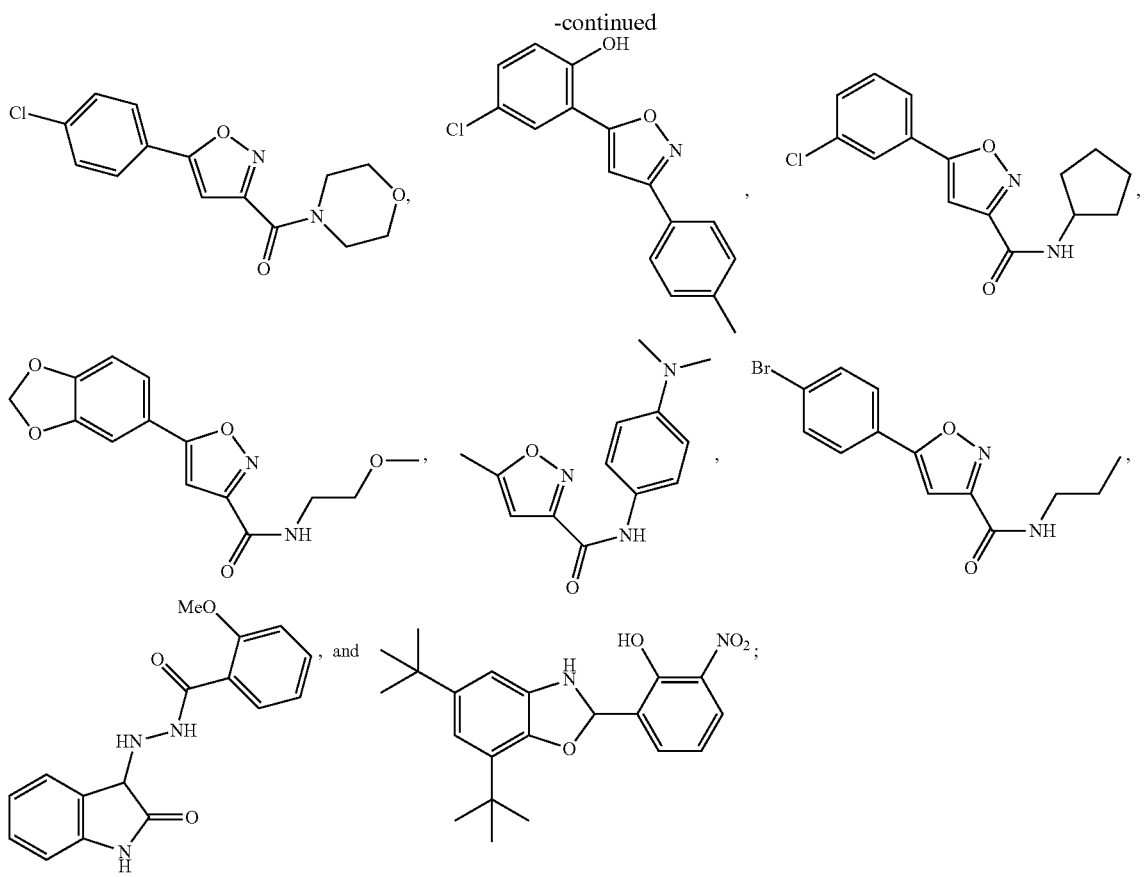

or a pharmaceutically acceptable salt thereof.

The step of administering may comprise intravenous, intra-arterial, subcutaneous or oral administration. Administering may also comprise daily administration, every other day administration, weekly administration or monthly administration The subject may be suspected of having frontotemporal dementia or have been diagnosed as having frontotempral dementia, such as by identification of a loss-of-function function mutation in said subject's progranulin gene. The method may further comprise administering to said subject a second treatment, such as a selective serotonin reuptake inhibitor. The subject may exhibit Tau pathology, TDP-43 pathology or FUS pathology.

The terms "contacted" and "exposed," when applied to a cell, are used herein to describe the process by which a compound of the disclosure is delivered to a target cell or is placed in direct juxtaposition with the target cell.

The term "effective," as that term is used in the specification and/or claims (e.g., "an effective amount," means adequate to accomplish a desired, expected, or intended result.

"Treatment" and "treating" as used herein refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease.

It is specifically contemplated that any limitation discussed with respect to one embodiment of the disclosure may apply to any other embodiment of the disclosure. Furthermore, any composition of the disclosure may be used in any method of the disclosure, and any method of the disclosure may be used to produce or to utilize any composition of the disclosure.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following figures form part of the present specification and are included to further demonstrate certain aspects of the present disclosure. The disclosure may be better understood by reference to one or more of these drawings in combination with the detailed description of specific embodiments presented herein.

(FIG. 1A) Cells were treated with Isoxazole in increasing concentrations ranging from 10 nM to 25 μM. Luciferase activity in cells shows a significant increase over control and decreases in a dose dependent manner. (FIG. 1B) Primary rat neurons were treated for 24 hours with DMSO and two concentrations of Isoxazole to visualize the increase in Progranulin protein expression in the relevant in vivo cell type. Treatment showed a significant increase over the DMSO control of protein levels in a dose dependent manner. Lower band: actin control. Bands at ~75 kDa: Progranulin monomer. HMW bands: Progranulin multimers. Densitometric quantitation is shown on the right.

DESCRIPTION OF ILLUSTRATIVE EMBODIMENTS

Figure 1A:
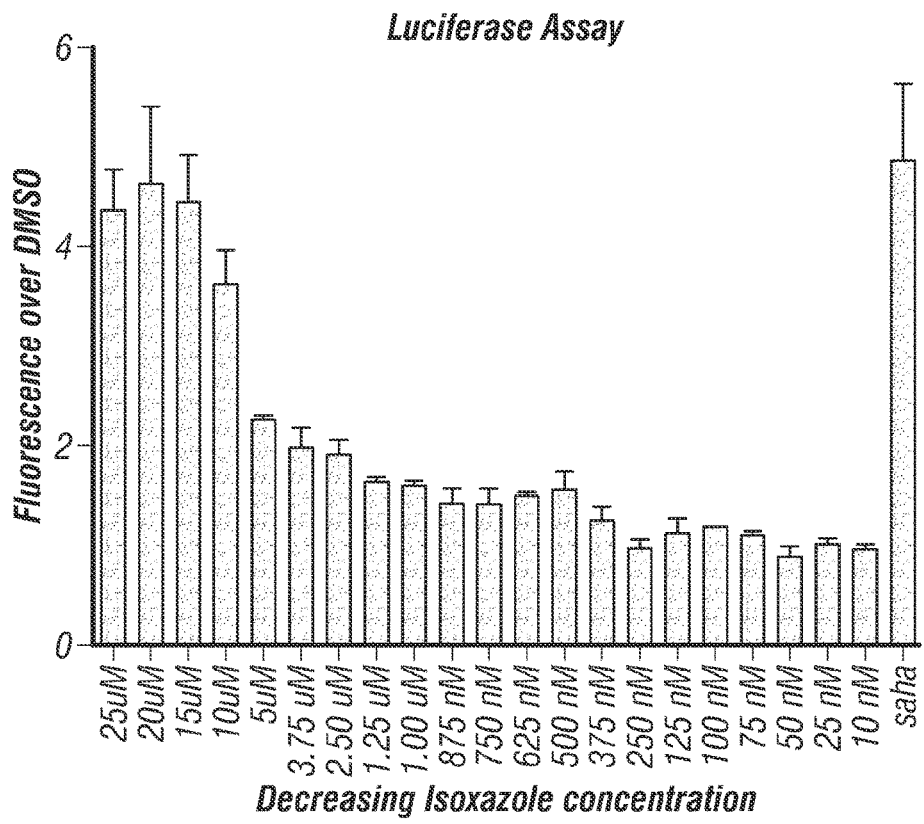
FIGS. 1A-B. Neuro2A #48 cells show a marked increase in Progranulin levels due to Isoxazole treatment after 24 hours.

Prograulin haploinsufficiency is the cause of one particular form of frontotemporal lobar degeneration (FTLD), frontotemporal dementia, or FTD. Using a prograulin promoter-driven luciferase reporter construct in a high throughput screen of small molecule library at the University of Texas Southwestern Medical Center, the inventors identified compounds that increase transcription from the prograulin promoter. A large number of compounds were identified, many of which exhibited activity to an extent that exceeds the clinical requirement for correcting diminished progranulin expression in mutation carriers. In particular, a class of 3,5-disubstituted isoxazoles was identified as having particular activity toward the progranulin promoter. These, and other aspects of the disclosure, are set out in detail below.

A. Compounds of the Present Disclosure

Compounds of the present disclosure may be considered as derived from isoxazoles. The following compounds are representative of certain compounds of the present disclosure:

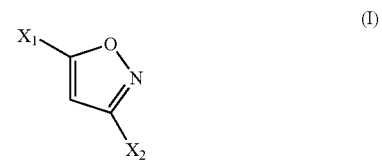

(I)

wherein:

$X_1$ is alkyl$_{(C \leq 12)}$ or heteroaryl$_{(C \leq 12)}$, or a substituted version of any of these groups; or $X_1$ is

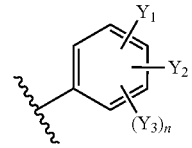

wherein $Y_1$ and $Y_2$ are each independently selected from hydrogen, halo, hydroxy, amino, nitro, or cyano, or alkyl$_{(C \leq 12)}$, alkoxy$_{(C \leq 12)}$, alkylamino$_{(C \leq 12)}$, dialkylamino$_{(C \leq 12)}$, or $Y_1$ and $Y_2$ are taken together to form

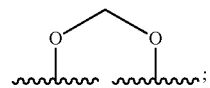 [SMILES: *OCO*]

$Y_3$ is hydrogen, halo, hydroxy, amino, nitro, cyano, mercapto, or phosphate; alkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, alkyloxy$_{(C \leq 12)}$, alkenyloxy$_{(C \leq 12)}$, alkynyloxy$_{(C \leq 12)}$, aryloxy$_{(C \leq 12)}$, heteroaryloxy$_{(C \leq 12)}$, aralkyloxy$_{(C \leq 12)}$, acyloxy$_{(C \leq 12)}$, alkylamino$_{(C \leq 12)}$, dialkylamino$_{(C \leq 12)}$, alkenylamino$_{(C \leq 12)}$, alkynylamino$_{(C \leq 12)}$, arylamino$_{(C \leq 12)}$, heteroarylamino$_{(C \leq 12)}$, aralkylamino$_{(C \leq 12)}$, amido$_{(C \leq 12)}$, alkylsulfonylamino$_{(C \leq 12)}$, alkylsulfonyl$_{(C \leq 12)}$, arylsulfonyl$_{(C \leq 12)}$, or a substituted version of these groups; and n is 1, 2, or 3; and $X_2$ is aryl$_{(C \leq 12)}$, substituted aryl$_{(C \leq 12)}$, or —C(O)NR$_1$R$_2$; wherein $R_1$ and $R_2$ are independently selected from hydrogen, alkyl$_{(C \leq 12)}$, substituted alkyl$_{(C \leq 12)}$, alkenyl$_{(C \leq 12)}$, substituted alkenyl$_{(C \leq 12)}$, alkynyl$_{(C \leq 12)}$, substituted alkynyl$_{(C \leq 12)}$, aryl$_{(C \leq 12)}$, substituted aryl$_{(C \leq 12)}$, heteroaryl$_{(C \leq 12)}$, substituted heteroaryl$_{(C \leq 12)}$, aralkyl$_{(C \leq 12)}$, substituted aralkyl$_{(C \leq 12)}$, heteroaralkyl$_{(C < 12)}$, substituted heteroaralkyl$_{(C \leq 12)}$, or or -A-Y$_4$ wherein A is alkanediyl$_{(C \leq 12)}$ or substituted alkanediyl$_{(C \leq 12)}$ and Y$_4$ is

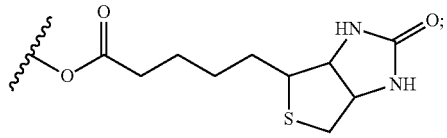 [SMILES: *OC(=O)CCCCC1SCC2NC(=O)NC21]

or when R$_1$ and R$_2$ are taken together, R$_1$ and R$_2$ are alkanediyl$_{(C \leq 12)}$, alkoxydiyl$_{(C \leq 12)}$, alkylaminodiyl$_{(C \leq 12)}$, or a substituted version of any of these groups; or a compound of the formula:

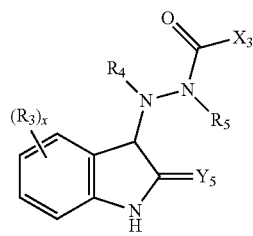
(II)

wherein:

X$_3$ is aryl$_{(C \leq 12)}$, heteroaryl$_{(C \leq 12)}$, or a substituted version of any of these groups; Y$_5$ is O, S, or NH; R$_3$ is amino, cyano, halo, hydroxy, nitro, hydroxysulfonyl, aminosulfonyl, alkyl$_{(C \leq 8)}$, substituted alkyl$_{(C \leq 8)}$, alkoxy$_{(C \leq 8)}$, substituted alkoxy$_{(C \leq 8)}$, acyl$_{(C \leq 8)}$, substituted acyl$_{(C \leq 8)}$, amido$_{(C \leq 8)}$, substituted amido$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$; x is 0, 1, 2, 3, or 4; and R$_4$ and R$_5$ are each independently selected from hydrogen, alkyl$_{(C \leq 6)}$, or substituted alkyl$_{(C \leq 6)}$; or a compound of the formula:

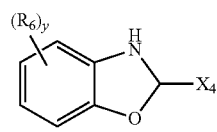
(III)

wherein: X$_4$ is aryl$_{(C \leq 12)}$, aralkyl$_{(C \leq 12)}$, heteroaryl$_{(C \leq 12)}$, or a substituted version of any of these groups; R$_6$ is amino, cyano, halo, hydroxy, nitro, hydroxysulfonyl, aminosulfonyl, alkyl$_{(C \leq 8)}$, substituted alkyl$_{(C \leq 8)}$, alkoxy$_{(C \leq 8)}$, substituted alkoxy$_{(C \leq 8)}$, acyl$_{(C \leq 8)}$, substituted acyl$_{(C \leq 8)}$, amido$_{(C \leq 8)}$, substituted amido$_{(C \leq 8)}$, alkylamino$_{(C \leq 8)}$, substituted alkylamino$_{(C \leq 8)}$, dialkylamino$_{(C \leq 8)}$, or substituted dialkylamino$_{(C \leq 8)}$; and y is 0, 1, 2, 3, 4; or a salt thereof.

TABLE 1

Example Compounds of the Invention

| Compound ID | Structure |
|---|---|
| C15 | 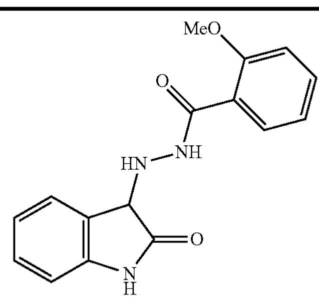 |
| C19 |  |

B. CHEMICAL DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "aminosulfonyl" means —S(O)$_2$NH$_2$; "hydroxysulfonyl" means —S(O)$_2$OH; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "====" represents a single bond or a double bond. Thus, for example, the formula includes

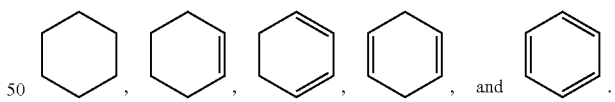

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol " ∿ ", when drawn perpendicularly across a bond (e.g., $$\xi\text{—CH}_3$$

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "⦀⦀⦀" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

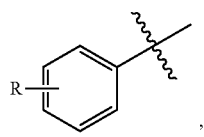

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

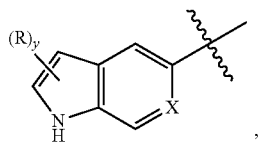

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C \leq 8)}$" or the class "alkene$_{(C \leq 8)}$" is two. For example, "alkoxy$_{(C \leq 10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$—(methylene), —CH$_2$CH$_2$—, —CH$_2$C(CH$_3$)$_2$CH$_2$—, —CH$_2$CH$_2$CH$_2$—, and

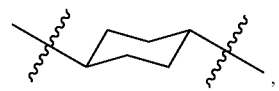 [SMILES: *C1CCC(*)CC1]

and are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, CH₂N(CH₃)₂, and —CH₂CH₂Cl. The term "haloalkyl" is a subset of substituted alkyl, in which one or more hydrogen atoms has been substituted with a halo group and no other atoms aside from carbon, hydrogen and halogen are present. The group, —CH₂Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH₂ (vinyl), —CH═CHCH₃, —CH═CHCH₂CH₃, —CH₂CH═CH₂ (allyl), —CH₂CH═CHCH₃, and —CH═CHCH═CH₂. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH═CH, —CH═C(CH₃)CH₂—, —CH═CHCH₂—, and

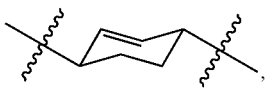 [SMILES: *C1C=CC(*)CC1]

are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups, —CH═CHF, —CH═CHCl and —CH═CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

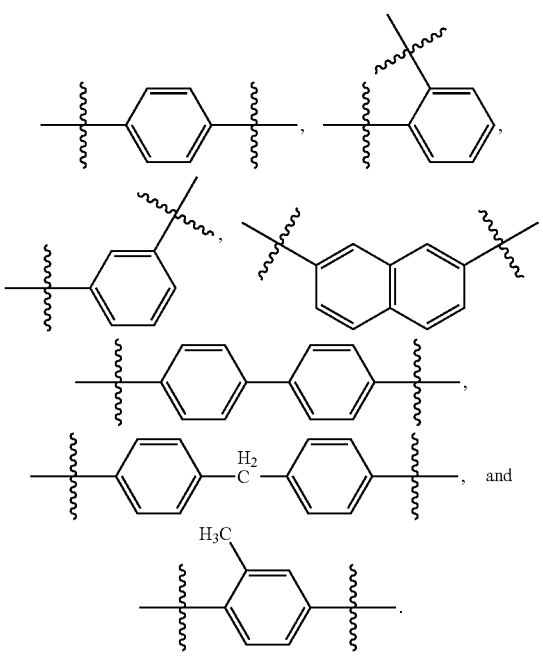

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

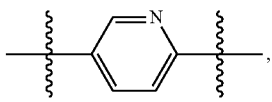

,

-continued

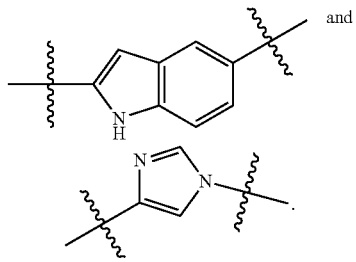

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, OC(O)CH$_3$, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of heteroaralkyls are: pyridylmethyl and thienylmethyl. When the term heteroaralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Non-limiting examples of substituted heteroaralkyls are: 2-chloroquinolylpropyl and 2-hydroxypyridylmethyl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused.

Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

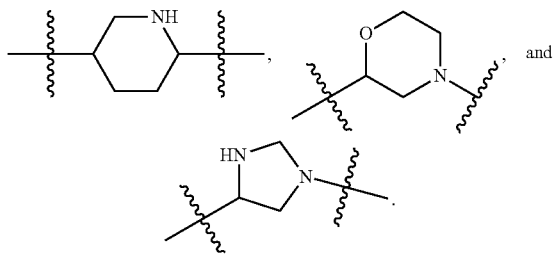

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

"Pharmaceutically acceptable salts" means salts of compounds of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis (3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

Modifications or derivatives of the compounds, agents, and active ingredients disclosed throughout this specification are contemplated as being useful with the methods and compositions of the present disclosure. Derivatives may be prepared and the properties of such derivatives may be assayed for their desired properties by any method known to those of skill in the art.

In certain aspects, "derivative" refers to a chemically modified compound that still retains the desired effects of the compound prior to the chemical modification. "Isoxazole derivatives," therefore, refers to a chemically modified compound that still retains the desired effects of the parent isoxazole prior to its chemical modification. Such effects may be enhanced (e.g., slightly more effective, twice as effective, etc.) or diminished (e.g., slightly less effective, 2-fold less effective, etc.) relative to the parent isoxazole, but may still be considered an isoxazole derivative. Such derivatives may have the addition, removal, or substitution of one or more chemical moieties on the parent molecule. Nonlimiting examples of the types modifications that can be made to the compounds and structures disclosed herein include the addition or removal of lower unsubstituted alkyls such as methyl, ethyl, propyl, or substituted lower alkyls such as hydroxymethyl or aminomethyl groups; carboxyl groups and carbonyl groups; hydroxyls; nitro, amino, amide, and azo groups; sulfate, sulfonate, sulfono, sulfhydryl, sulfonyl, sulfoxido, phosphate, phosphono, phosphoryl groups, and halide substituents. Additional modifications can include an addition or a deletion of one or more atoms of the atomic framework, for example, substitution of an ethyl by a propyl; substitution of a phenyl by a larger or smaller aromatic group. Alternatively, in a cyclic or bicyclic structure, heteroatoms such as N, S, or O can be substituted into the structure instead of a carbon atom.

Prodrugs and solvates of the compounds of the present disclosure are also contemplated herein. The term "prodrug" as used herein, is understood as being a compound which, upon administration to a subject, such as a mammal, undergoes chemical conversion by metabolic or chemical processes to yield a compound any of the formulas herein, or a salt and/or solvate thereof (Bundgaard, 1991; Bundgaard, 1985). Solvates of the compounds of the present disclosure are preferably hydrates.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the disclosure with an organic base such as methylamine, ethylamine, ethanolamine, lysine, ornithine and the like.

Pharmaceutically acceptable salts include the salts formed between carboxylate or sulfonate groups found on some of the compounds of this disclosure and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (2002), which is incorporated herein by reference.

As used herein, the term "cyclic group" refers to a carbocycle group (e.g., cyclopropyl, cyclohexyl), a heterocycle group (e.g., pyrrolidinyl), an aryl group, or any combination thereof (e.g., fused bicyclic group).

As used herein, "protecting group" refers to a moiety attached to a functional group to prevent an otherwise unwanted reaction of that functional group. Protecting groups are well-known to those of skill in the art. Non-limiting exemplary protecting groups fall into categories such as hydroxy protecting groups, amino protecting groups, sulfhydryl protecting groups and carbonyl protecting groups. Such protecting groups may be found in Greene and Wuts (1999). Compounds of the present disclosure are specifically contemplated wherein one or more functional groups are protected by a protecting group.

Compounds of the present disclosure may contain one or more asymmetric centers and thus can occur as racemates and racemic mixtures, single enantiomers, diastereomeric mixtures and individual diastereomers. In certain embodiments, a single diastereomer is present. All possible stereoisomers of the compounds of the present disclosure are contemplated as being within the scope of the present disclosure. However, in certain aspects, particular diastereomers are contemplated. The chiral centers of the compounds of the present disclosure can have the S- or the R-configuration, as defined by the IUPAC 1974 Recommendations. In certain aspects, certain compounds of the present disclosure may comprise S- or R-configurations at particular carbon centers. For example, the following specific compound contains an asymmetric center:

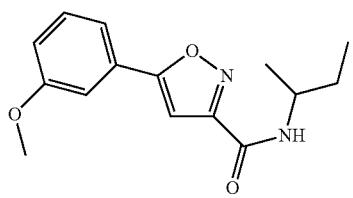 [SMILES: CCC(C)NC(=O)c1cc(-c2cccc(OC)c2)on1]

and are thus claimed as a racemic mixture, R, and S forms.

Solvent choices for the synthetic preparation of compounds of the present disclosure will be known to one of ordinary skill in the art. Solvent choices may depend, for example, on which one(s) will facilitate the solubilizing of all the reagents or, for example, which one(s) will best facilitate the desired reaction (particularly when the mechanism of the reaction is known). Solvents may include, for example, polar solvents and non-polar solvents. Solvents choices include, but are not limited to, tetrahydrofuran, dimethylformamide, dimethylsulfoxide, dioxane, methanol, ethanol, hexane, methylene chloride and acetonitrile. More than one solvent may be chosen for any particular reaction or purification procedure. Water may also be admixed into any solvent choice. Further, water, such as distilled water, may constitute the reaction medium instead of a solvent.

Persons of ordinary skill in the art will be familiar with methods of purifying compounds of the present disclosure. One of ordinary skill in the art will understand that compounds of the present disclosure can generally be purified at any step, including the purification of intermediates as well as purification of the final products. In particular embodiments, purification is performed via silica gel column chromatography or HPLC.

In view of the above definitions, other chemical terms used throughout this application can be easily understood by those of skill in the art. Terms may be used alone or in any combination thereof. The preferred and more preferred chain lengths of the radicals apply to all such combination.

C. Frontotemporal Dementia

Frontotemporal dementia (FTD), formerly known as disinhibition-dementia-parkinsonism-amyotrophy complex (DDPAC), is a neurodegenerative disease characterized by severe frontotemporal lobar degeneration. The disorder was first identified in 1994 by Kirk Wilhelmsen and colleagues, who distinguished it from Alzheimer's disease and Lewy body dementia based on the fact that it did not manifest with amyloid plaques, neurofibrillary tangles, or Lewy bodies. Second only to Alzheimer's disease (AD) in prevalence, FTD accounts for 20% of pre-senile dementia cases. Symptoms can begin to appear on average around 45 to 65 years of age, regardless of gender. The most common symptoms include significant changes in social and personal behavior, as well as a general blunting of emotions. Symptoms progress at a rapid, steady rate. Patients suffering from the disease can survive between 2-10 years. Eventually patients will need 24-hour care for daily function. Because FTD often occurs in younger people (i.e., in their 40's or 50's), it can severely affect families. Patients often still have children living in the home. Financially, it can be devastating as the disease strikes at the time of life that is often the top wage-earning years. Currently, there is no cure for FTD. Treatments are available to manage the behavioral symptoms. Disinhibition and compulsive behaviors can be controlled by selective serotonin reuptake inhibitors (SSRIs). Although Alzheimer's and FTD share certain symptoms, they cannot be treated with the same pharmacological agents because the cholinergic systems are not affected in FTD.

FTD is traditionally difficult to diagnose due to the heterogeneity of the associated symptoms. Symptoms are classified into three groups based on the functions of the frontal and temporal lobes. Behavioral variant FTD (bvFTD) exhibits symptoms of lethargy and aspontaneity on the one hand, and disinhibition on the other. Apathetic patients may become socially withdrawn and stay in bed all day or no longer take care of themselves. Disinhibited patients can make inappropriate (sometimes sexual) comments or perform inappropriate acts. Patients with FTD can sometimes get into trouble with the law because of inappropriate behavior such as stealing or speeding. Recent findings indicate that psychotic symptoms are rare in FTD, possibly due to limited temporal-limbic involvement. Among FTD patients, approximately 2% have delusions, sometimes with paranoid ideation. Hallucinations are rare. These psychotic symptoms are significantly less prevalent than what is seen in AD patients, where approximately 20% have delusions and paranoia. Progressive nonfluent aphasia (PNFA) presents with a breakdown in speech fluency due to articulation difficulty, phonological and/or syntactic errors but preservation of word comprehension. Semantic dementia (SD) can be found in some patients that remain fluent with normal phonology and syntax, but increasing difficulty with naming and word comprehension. It has been researched that some may even go through depression and lose their inhibitions and exhibit antisocial behavior.

FTD patients tend to struggle with binge eating and compulsive behaviors. These binge eating habits are often associated with abnormal eating behavior including overeating, stuffing oneself with food, changes in food preferences (cravings for more sweets, carbohydrates), eating inedible objects and snatching food from others. Recent findings have indicated that the neural structures responsible for eating changes in FTD include atrophy in the right ventral insula, striatum and orbitofrontal cortex on structural MRI voxel-based morphometry (right hemisphere).

Executive function is the cognitive skill of planning and organizing. Most FTD patients become unable to perform skills that require complex planning or sequencing. In addition to the characteristic cognitive dysfunction, a number of primitive reflexes known as frontal release signs are often able to be elicited. Usually, the first of these frontal release signs to appear is the palmomental reflex which appears relatively early in the disease course whereas the palmar grasp reflex and rooting reflex appear late in the disease course. The following abilities in the FTD patients are preserved: perception, spatial skills, memory, praxis, The following abilities in FTD patients are affected: social behavior/conduct, regulation of emotion, ability to focus, utilization behavior (neurobehavioral disorder where the patients grab objects in view and start to conduct the right behavior at the wrong time), and inappropriate speech/actions.

In rare cases, FTD can occur in patients with motor neuron disease (MND) (typically amyotrophic lateral sclerosis). The prognosis for people with MND is worse when combined with FTD, shortening survival by about a year. A number of case series have now been published looking at the pathological basis of frontotemporal dementia. As with other syndromes associated with frontotemporal lobar degeneration (FTLD), a number of different pathologies are associated with FTD:

Tau pathology: In a healthy individual, tau proteins stabilize microtubules, which are major component of the cytoskeleton. Examples include Pick's disease, now also referred to as FTLD-tau, and other tau-positive pathology including FTDP-17, corticobasal degeneration, and progressive supranuclear palsy. Approximately 50% of FTD cases will present with tau pathology at post-mortem.

TDP-43 pathology: This disease form was previously described as dementia with ubiquitin positive, tau- and alpha-synuclein negative inclusions with and without motor neuron degeneration. FTLD-TDP43 accounts for approximately 40% of FTD (±MND).

FUS pathology: Cases with underlying FUS pathology tend to present with behavioural variant FTD (bvFTD), but the correlation is by no means reliable enough to predict the post mortem pathology. FTLD-FUS represents only 5-10% of clinically diagnosed FTD.

Dementia lacking distinctive histology (DLDH) is a rare entity and represents the remaining small percentage of FTD that cannot be positively diagnosed as any of the above at post-mortem.

In rare cases, patients with clinical FTD were found to have changes consistent with Alzheimer's disease on autopsy Evidence suggests that FTD selectively impairs spindle neurons, a type of neuron which has only been found in the brains of humans, great apes, and whales. Deficiencies of the micronutrients folate and B12 have been associated with cognitive impairment in individuals with FTD. Chronic folate deficiency has also been implicated in cerebral atrophy, leading to neurological impairment.

Structural MRI scans often reveal frontal lobe and/or anterior temporal lobe atrophy but in early cases the scan may seem normal. Atrophy can be either bilateral or asymmetric. Registration of images at different time points of time (e.g., one year apart) can show evidence of atrophy that otherwise (at individual time points) may be reported as normal. Many research groups have begun using techniques such as magnetic resonance spectroscopy, functional imaging and cortical thickness measurements in an attempt to offer an earlier diagnosis to the FTD patient. Fluorine-18-Fluorodeoxyglucose Positron Emission Tomography (FDG-PET) scans classically show frontal and/or anterior temporal hypometabolism, which helps differentiate the disease from Alzheimer's disease. The PET scan in Alzheimer's disease classically shows biparietal hypometabolism. Meta-analyses based on imaging methods have shown that frontotemporal dementia mainly affects a frontomedial network discussed in the context of social cognition or 'theory of mind'. This is entirely in keeping with the notion that on the basis of cognitive neuropsychological evidence, the ventromedial prefrontal cortex is a major locus of dysfunction early on in the course of the behavioural variant of frontotemporal degeneration. The language subtypes of frontotemporal lobar degeneration (semantic dementia and progressive nonfluent aphasia) can be regionally dissociated by imaging approaches in vivo.

The confusion between Alzheimer's and FTD is justifiable due to the similarities between their initial symptoms. Patients do not have difficulty with movement and other motor tasks. As FTD symptoms appear, it is difficult to differentiate between a diagnosis of Alzheimer's disease and FTD. There are distinct differences in the behavioral and emotional symptoms of the two dementias, notably, the blunting of emotions seen in FTD patients. In the early stages of FTD, anxiety and depression are common, which may result in an ambiguous diagnosis. However, over time, these ambiguities fade away as this dementia progresses and defining symptoms of apathy, unique to FTD, start to appear.

In vivo brain imaging of tau aggregation in frontotemporal dementia using [F-18]FDDNP positron emission tomography is more visual and has enhanced the ability to have a deeper understanding in frontal temporal dementia. Previous fluorescent microscopy studies of Alzheimer's disease (AD) brain specimens have shown that [F-18] FDDNP displays an excellent visualization of interneuronal neurofibrillary tangles (NFTs). Visual images of [F-18]FDDNP-PET images emphasized a frontal signal in FTD compared to prominent temporal signals in AD. [F-18]FDDNP-PET has allowed the enhanced visualization of tauopathies in patients. This has aided in differentiating FTD from parietal and temporal signals in AD. Further, the ability of [F-18] FDDNP to entitle tauopathies in vivo gives a tool for monitoring the effect of therapies to eliminate NFT accumulation. Recent studies over several years have developed new criteria for the diagnosis of behavioral variant frontotemporal dementia (bvFTD). Six distinct clinical features have been identified as symptoms of bvFTD:

Disinhibition
Apathy/Inertia
Loss of Sympathy/Empathy
Perseverative/compulsive behaviors
Hyperorality
Dysexecutive neuropsychological profile Of the six features, three must be present in a patient to diagnose one with possible bvFTD. Similar to standard FTD, the primary diagnosis stems from clinical trials that identify the associated symptoms, instead of imaging studies. The above criteria are used to distinguish bvFTD from disorders such as Alzheimer's and other causes of dementia. In addition, the new criteria allow for a diagnostic hierarchy distinguished possible, probable, and definite bvFTD based on the number of symptoms present.

A higher proportion of FTD cases seem to have a familial component than more common neurodegenerative diseases like Alzheimer's disease. More and more mutations and genetic variants are being identified all the time, so the lists of genetic influences require consistent updating. Tau-positive frontotemporal dementia with parkinsonism (FTDP-17) is caused by mutations in the MAPT gene on chromosome 17 that encodes the Tau protein It has been determined that there is a direct relationship between the type of tau mutation and the neuropathology of gene mutations. The mutations at the splice junction of exon 10 of tau lead to the selective deposition of the repetative tau in neurons and glia. The pathological phenotype associated with mutations elsewhere in tau is less predictable with both typical neurofibrillary tangles (consisting of both 3 repeat and 4 repeat tau) and Pick bodies (consisting of 3 repeat tau) having been described). The presence of tau deposits within glia is also variable in families with mutations outside of exon 10. This disease is now informally designated FTDP-17T. FTD shows a linkage to the region of the tau locus on chromosome 17, but it is believed that there are two loci leading to FTD within megabases of each other on chromosome 17. FTD caused by FTLD-TDP43 has numerous genetic causes. Some cases are due to mutations in the GRN gene, also located on chromosome 17. Others are caused by VCP mutations, although these patients present with a complex mixture of Inclusion body myopathy, Paget's disease of bone, and FTD. The most recent addition to the list is a hexanucleotide repeat expansion in the promotor region of C9ORF72. Only one or two cases have been reported describing TARDBP (the TDP-43 gene) mutations in a clinically pure FTD (FTD without MND).

D. Pharmaceutical Compositions and Treatments

Clinical applications require preparing of pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render materials stable and allow for uptake by target cells. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, intrathecal or intravenous injection. Such compositions would normally be administered as pharmaceutically acceptable compositions, described supra. The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present disclosure may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

E. Examples

The following examples are included to demonstrate certain preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Materials and Methods

Reagents and Antibodies. Cell culture reagents and TRIzol® were from Invitrogen. Rabbit antibodies were generated against linker-3 anti-mouse progranulin peptide ((C)VPWMKKVIAPLRLPDPQIL (SEQ ID NO: 1), amino acid residues 353-371) conjugated to keyhole limpet hemocyanin.

Plasmids and Cell Lines. The firefly luciferase coding sequence was fused by bacterial recombination to the authentic human GRN start codon in exon 2 (NM_002087.2) on a bacterial artificial chromosome (BAC-PAC RP11-812N09), and stably transfected Neuro-2a cells were derived.

Cell Culture and Drug Treatments. Neuro-2a and HEK293 cells were grown in DMEM and 10% FBS. Sodium valproate was dissolved in PBS. All other drugs were dissolved in DMSO (10-50 mM stock solutions kept at −80° C.) and diluted in cell culture medium to a final DMSO concentration of 0.2-0.5%.

Human Cell Lines. All experiments pertaining to collection of human samples were approved by the University of California San Francisco Committee on Human Research. The human subjects and family members were recruited at the University of California San Francisco Memory and Aging Center, and written informed consent was obtained. Genotypes were confirmed by direct sequencing. To obtain human dermal fibroblasts, skin biopsy samples were cut into small pieces, placed under a coverslip, and grown in DMEM containing glutamine, sodium pyruvate, nonessential amino acids, 10% FBS, penicillin, streptomycin, and amphotericin B for ~3 weeks. Amphotericin B was omitted for further passages. The cells were used at passage 3 or 4.

Immortalized human lymphoblastoid cells were prepared as described (15). Briefly, white blood cells were obtained by Ficoll gradient centrifugation of the Buffy coat from donor blood and transformed in growth medium containing 25% FCS, 1% phytohemagglutinin, and 10% Epstein-Barr virus supernatant. Rapidly growing cultures were maintained in RPMI 1640 medium and 10% FBS.

Library Screening and Luciferase Reporter Assays. Neuro-2a cells were assayed in 384-well plates (3000 cells/well). 6 hrs after cell plating, 1200 Prestwick Chemical Library® compounds in DMSO, including internal controls, were dispensed using a BioMek FX system to final concentrations of 2.5 µM compound and 1% DMSO (unless indicated otherwise). Sodium butyrate (9 mM) was used as a positive control on each plate for initial screening. Luciferase activity was measured 24 hr after compound addition using Bright-Glo™ reagent (20 µl/well; Promega). Each well was normalized to the average luminescence from DMSO-treated wells on the same plate.

Determination of Cell Viability. Neuro-2a cells were seeded in 384-well plates (3000 cells/well). After 24 hr of drug treatment, the ATP content of each well was measured with the CellTiter-Glo® luminescent cell viability assay (Promega) according to the manufacturer's instructions.

RNA Extraction and Quantitative PCR. Cells in 6-well plates were lysed in 500 µl of TRIzol® reagent/well. cDNA was reverse-transcribed with MultiScribe™ (Applied Biosystems). For some experiments, the Quick-RNA MiniPrep system (Zymo Research, Irvine, Calif.) was used to isolate total RNA. Primer sequences were as follows:

```
human U36B-F,
                                  (SEQ ID NO: 2)
5'-CGAGGGCACCTGGAAAAC-3';

human U36B-R,
                                  (SEQ ID NO: 3)
5'-CACATTCCCCCGGATATGA-3';

human GRN-S,
                                  (SEQ ID NO: 4)
5'-CAGGGACTTCCAGTTGCTGC-3';

human GRN-A,
                                  (SEQ ID NO: 5)
5'-GCAGCAGTGATGGCCATCC-3';

mouse cyclophilin QF1S,
                                  (SEQ ID NO: 6)
5'-GGAGATGGCACAGGAGGAA-3';

mouse cyclophilin QR1A,
                                  (SEQ ID NO: 7)
5'-GCCCGTAGTGCTTCAGCTT-3';

mouse GRNS,
                                  (SEQ ID NO: 8)
5'-AGTTCGAATGTCCTGACTCCGCCA-3';

mouse GRNA,
                                  (SEQ ID NO: 9)
5'-AAGCCACTGCCCTGTTGGTCCTTT-3';

intronic GRN_F1,
                                  (SEQ ID NO: 10)
5'-CCGGCTACTGTCCAGAGGTCC-3';
and intronic GRN_R1,
                                  (SEQ ID NO: 11)
5'-CTAGGGGAGTTTCAAGAGGCAGGT-3'.
```

Quantitative PCRs (qPCRs; 10 µl) contained 20 ng of cDNA, 150 nM primer, and 5 µl of Fast SYBR Green PCR Master Mix (Applied Biosystems) and were performed in triplicate on an Applied Biosystems PRISM 7500 Fast sequence detection system. Relative mRNA levels were calculated using U36B or cyclophilin Q primers as internal controls.

Immunoblotting and Quantification. Cells were lysed in radioimmune precipitation assay buffer (50 mM Tris-HCl (pH 7.4), 150 mM NaCl, 1 mM EDTA, 1% Triton X-100, 1% sodium deoxycholate, 0.1% SDS, and Roche Complete protease inhibitor mixture) and cleared by centrifugation at 20,000×g for 10 min. 0.5-ml cell culture supernatants containing 1% FBS were concentrated by centrifugation at 14,000×g for 50 min in Millipore Amicon Ultra devices (3-kDa cutoff). 15-20 µg of total protein was separated by SDS-PAGE and transferred to nitrocellulose membranes. Membranes were blocked in 5% milk for 1 hr and probed overnight with primary antibodies at 4° C. Mouse progranulin was detected with linker-3 anti-progranulin antibody at 1:5000 dilution, β-actin with anti-β-actin antibody (Sigma A2228) at 1:5000 dilution, human progranulin with anti-PC cell-derived growth factor antibody (Invitrogen) at 1:1000 dilution, and GAPDH with anti-GAPDH antibody (Sigma) at 1:10,000 dilution. Bound IgG was detected by ECL. For quantitative immunoblotting, secondary antibodies labeled with IRDye® infrared dyes and an Odyssey® infrared imager (LI-COR Biosciences) were used following the manufacturer's instructions.

Statistical Analysis. Statistical analysis was done with SigmaPlot 11 software. For comparison between multiple treatment groups, analysis of variance was followed by Dunnett's or Tukey's test. All data are presented as means±S. E.

Technical details of HTS screen. Cell type used: Neuro-2a #48 cell line was cultured in DMEM (High glucose)/10%FBS/Pen-Strep/Zeocin (200 µg/mL) and plated in same media without Zeocin. All media is sterile filtered before use. The firefly luciferase coding sequence was fused by bacterial recombination to the authentic human GRN start codon in exon 2 (NM_002087.2) on a bacterial artificial chromosome (BACPAC RP11-812N09), and stably transfected Neuro-2a cells were derived (Cenik et al., 2011). Cells are put into single cell suspension and strained with 70 µm cell strainers before counting. The concentration of cells is adjusted to 150,000 cells/ml.

384 well plates were used for the assay: 50 µL of the cell suspension are added to each well for a final cell number per well of 7,500. Plates are spun down after plating and incubated at 37° C. under 5% $CO_2$. Compound addition takes place 4 hours after plating. Test compounds are in columns 3-22. The vehicle control wells are in columns 2 and 23. The positive control, SAHA (3 µM), is plated in column 1 An untreated control (no DMSO) is in column 24. The plates are assayed for reporter activity 24 hrs after compound addition. All media is spun out of the plates and 20 µL of bright glo is added to each well and placed on shaker for 3-5 minutes. After shaking, plates are read and check from increases in activation over DMSO. Vehicle (DMSO) was used for baseline because it causes a slight activation of luciferase construct. SAHA showed an activation of 4-5 times base line. All compounds were added from DMSO stocks and added at 0.5 µL per well (1% DMSO). All plates are read on an EnVision multilabel plate reader in luminescence mode. The data is then parsed into GeneData Screener v11 and quality controlled visually. Z' values are calculated using the DMSO and SAHA controls. Plates that have a Z' value less than 0.45 are further scrutinized. If the latter show systematic effects or if known errors occurred in these plates, they are repeated in a separate experiment. Data are then normalized and analyzed as previously described (Kim et al., 2013).

Example 2

Results

Figure 1B:
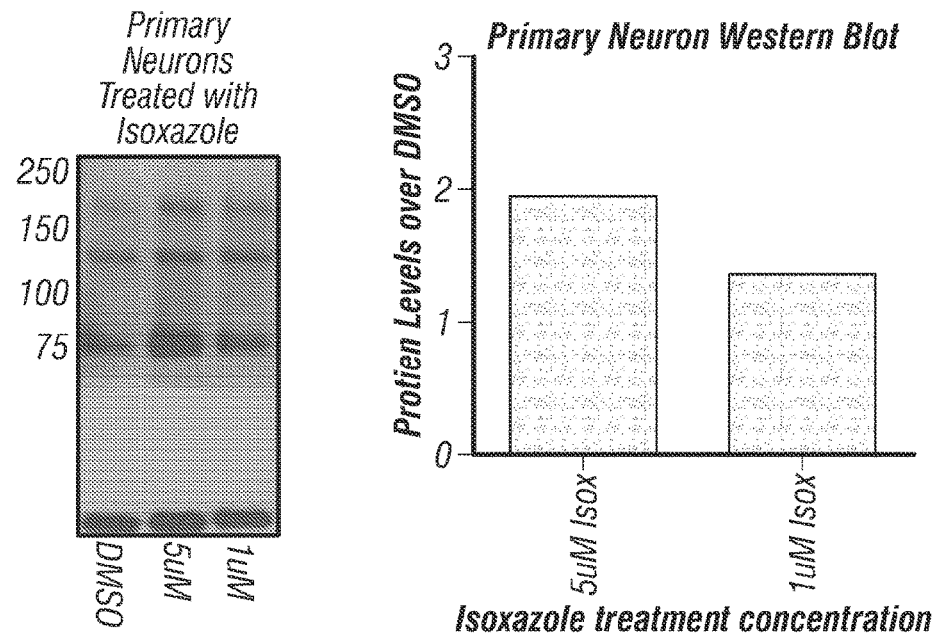
Figure 2:
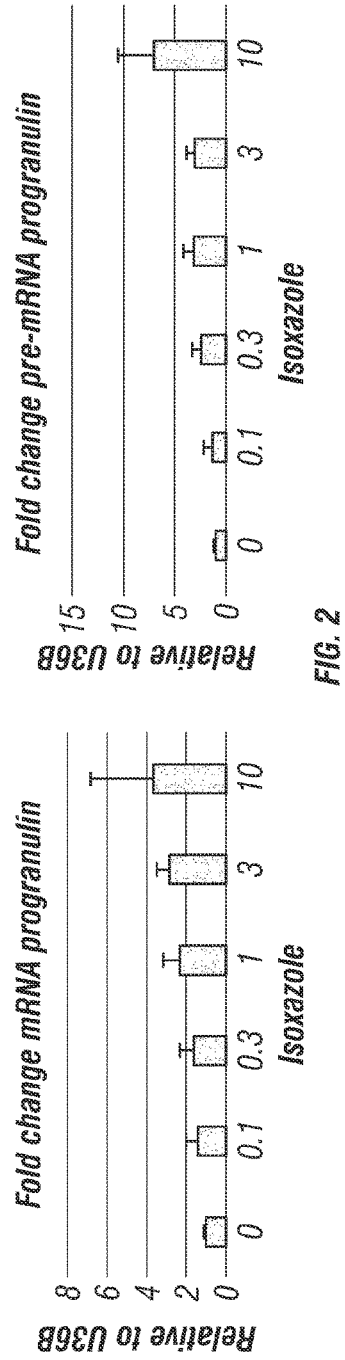
FIG. 2. Neuro2A cells were treated for 48 hours with increasing concentrations of Isoxazole. RT PCR was conducted to measure increases in progranulin mRNA and pre-mRNA (hnRNA before splicing). Both mRNA and pre-mRNA showed significant increases in a dose dependent manner.

FIG. 1A shows the effects of isoxazole treatment on Neuro2A #48 cells. The compound caused a marked increase in Progranulin levels after 24 hours at concentrations ranging from 10 nM to 25 µM. Luciferase activity in cells shows a significant increase over control and decreases in a dose dependent manner. FIG. 1B shows primary rat neurons treated for 24 hours with DMSO and two concentrations of Isoxazole to visualize the increase in Progranulin protein expression in the relevant in vivo cell type. The reatment showed a significant increase over the DMSO control of protein levels in a dose dependent manner. FIG. 2 shows Neuro2A cells treated for 48 hours with increasing concentrations of Isoxazole and RT PCR conducted to measure increases in progranulin mRNA and pre-mRNA (hnRNA before splicing). Both mRNA and pre-mRNA showed significant increases in a dose dependent manner.

Figure 3:
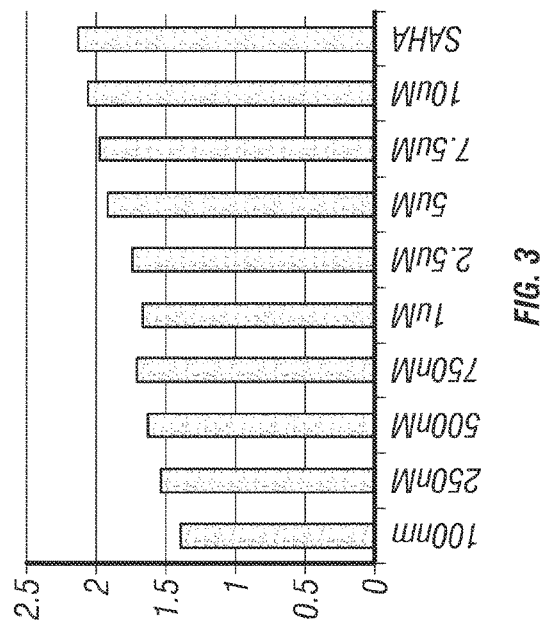
FIG. 3. Neuro 2 A #48 cells show increasing levels of luciferase activity over DMSO control when treated with increasing concentrations of sphingosinephosphorylcholine, a putative physiological ligand for GPR68. Isoxazoles are thought to activate and signal through GPR68. This finding further suggests that Progranulin is being regulated physiologically through pathways involving G-protein coupled receptors, specifically GPR68 and potentially other members of the same family.
Figure 4:
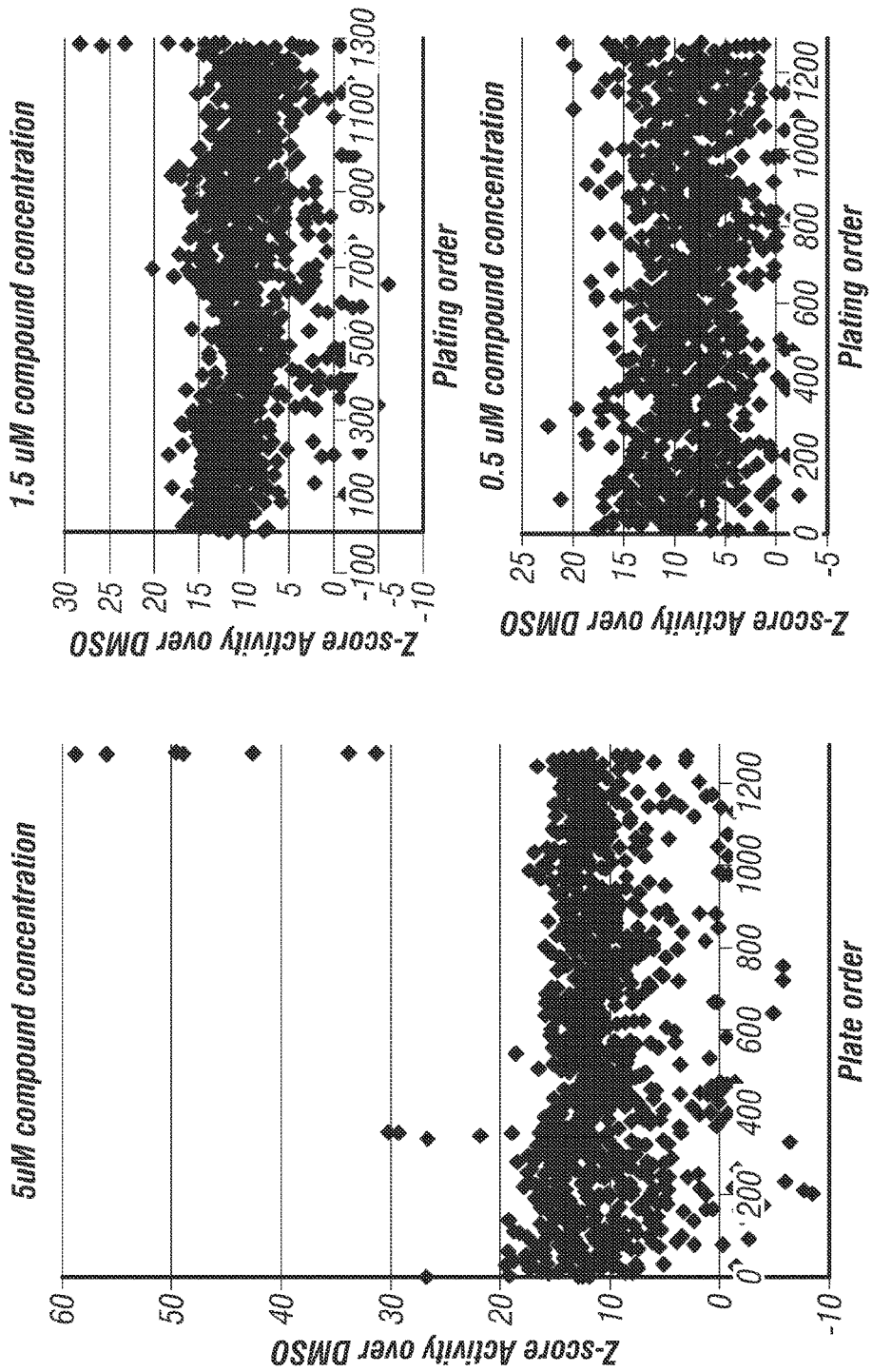
FIG. 4. Confirmation screen of top 1280 compounds found in the original 200,000 compound screen. Compound activity is determined based on robust Z-score calculated by the screening core using proprietary plate algorithms.

FIG. 3 shows that isoxazole treatment of Neuro 2 A #48 cells increased levels of luciferase activity over DMSO control when treated with increasing concentrations of sphingosinephosphorylcholine, a putative physiological ligand for GPR68. Isoxazoles are thought to activate and signal through GPR68. This finding further suggests that Progranulin is being regulated physiologically through pathways involving G-protein coupled receptors, specifically GPR68 and potentially other members of the same family. FIG. 4 shows a confirmation screen of top 1280 compounds found in the original 200,000 compound screen. Compound activity is determined based on robust Z-score calculated by the screening core using proprietary plate algorithms.

Figure 5A:
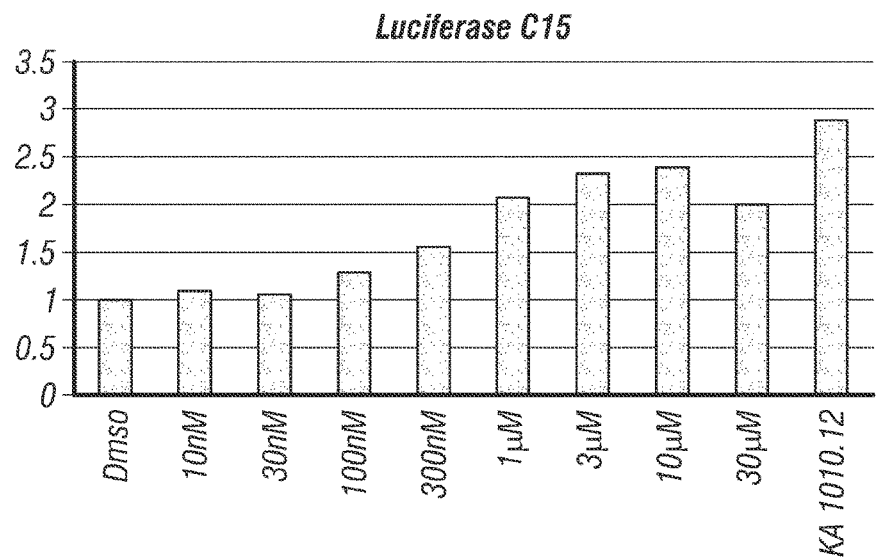
FIG. 5A & 5B. Luciferase Assay Data. Activity of compound C15 (FIG. 5A) and compound C19 (FIG. 5B) in Neuro2A #48 cells.
Figure 5B:
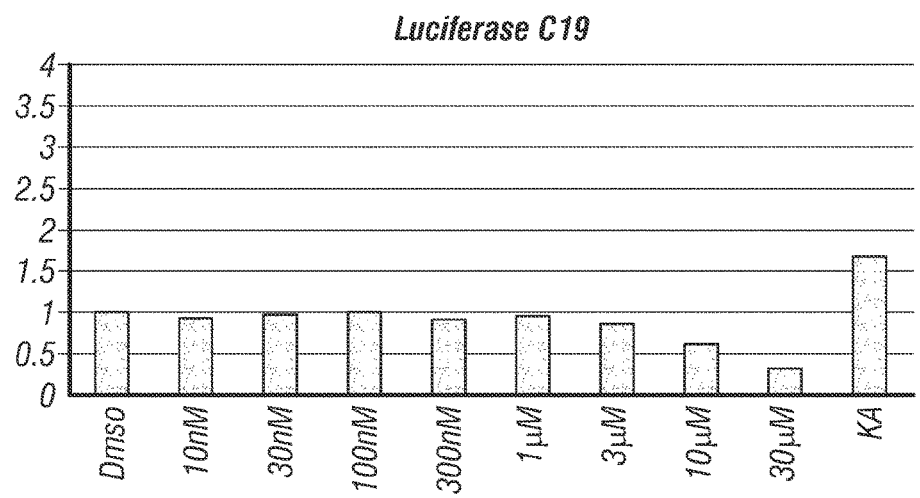

Both compounds (C15 and C19) were tested for increased luciferase activity in our Neuro2A #48 cells (FIGS. 5A & 5B). C15 showed a dose dependent increase in luciferase activity while C19 showed only a small change.

Figure 6:
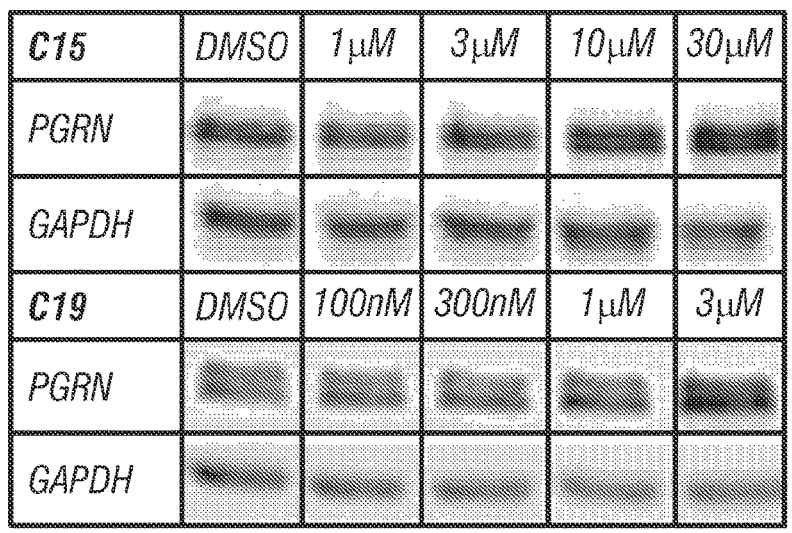
FIG. 6. Protein analysis using immuoblotting. Neuro2a cells were treated with in increasing doses for 48 hours and whole cell lysates were analyzed for progranulin (PGRN) protein expression using immunobloting. N=4.
Figure 7:
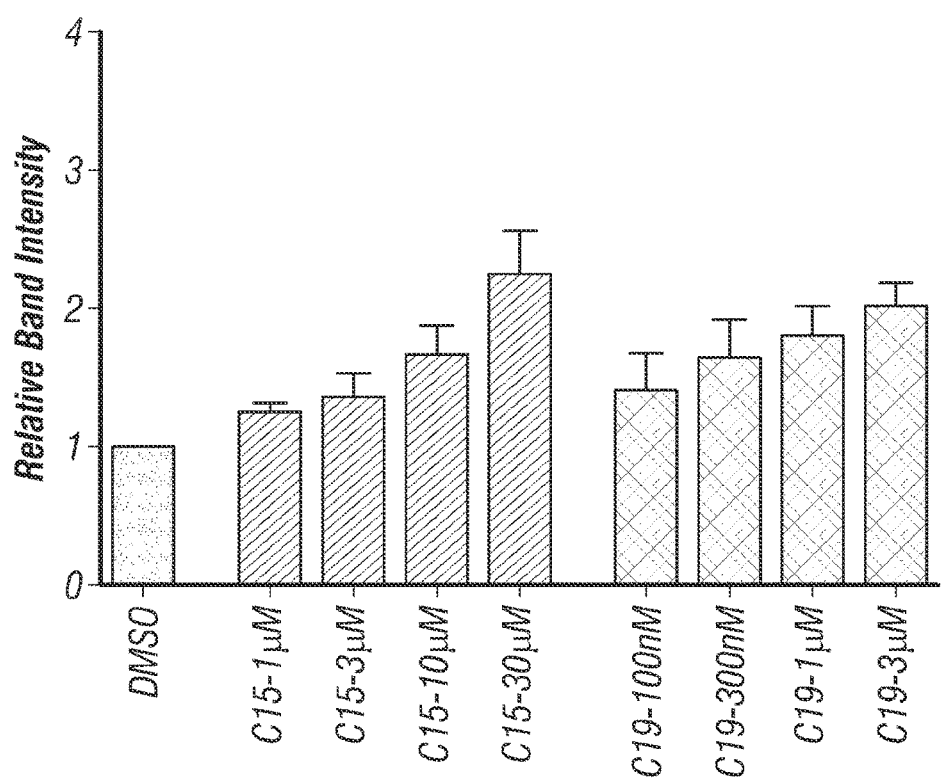
FIG. 7. Graphical analysis of protein quantification using immunoblotting. Whole cell lysates were analyzed for progranulin (PGRN) protein expression using immunoblotting and were graphically plotted to show changes in band intensity. PGRN levels doubled compared to DMSO at the highest concentrations. N=4.
Figure 8A:
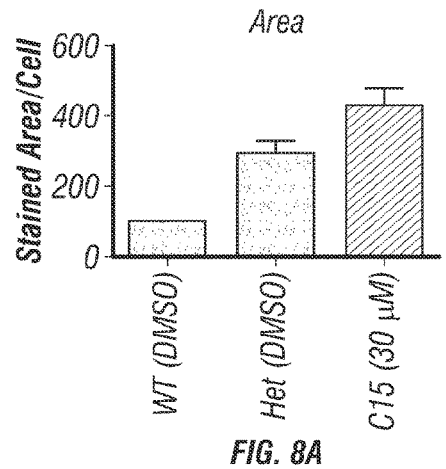
FIGS. 8A-8F. Dose Tested for Lysosome Rescue. Progranulin MEF cells were treated with 1 concentration each of C15 and C19 and levels of lysotracker were analyzed to look for reduction of lysosome levels back to wild type levels. The stained area per cell is measured for compound C15 (FIG. 8A) and C19 (FIG. 8B), area intensity for compound C15 (FIG. 8C) and C19 (FIG. 8D), and total number of lysosomes for compound C15 (FIG. 8E) and C19 (FIG. 8F).
Figure 8B:
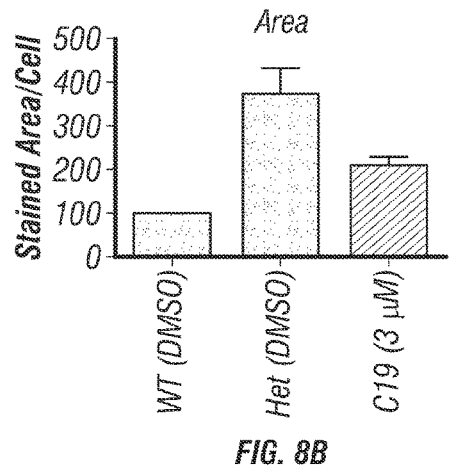
Figure 8C:
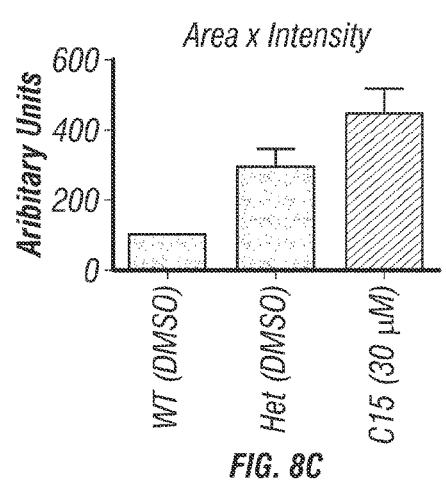
Figure 8D:
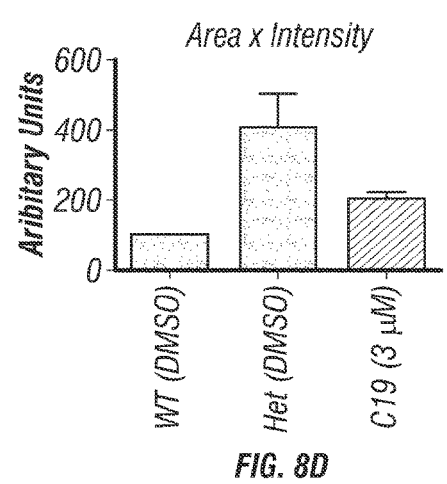
Figure 8E:
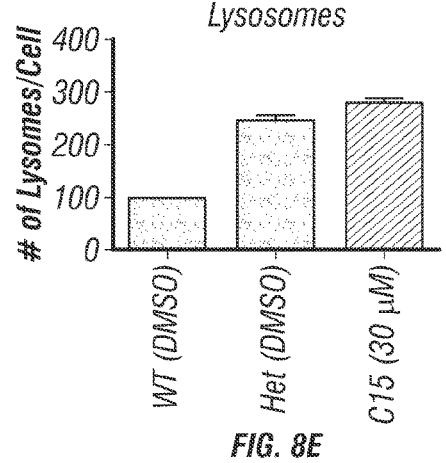
Figure 8F:
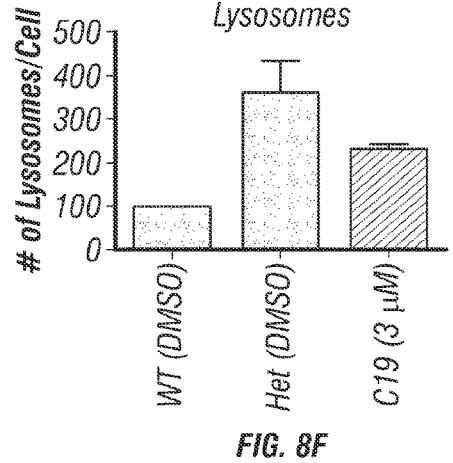

C15 and C19 increased progranulin protein levels in Neuro2a cells as measured by immunoblotting. Neuro2a cells were treated with in increasing doses for 48 hours and whole cell lysates were analyzed for progranulin (PGRN) protein expression using immunoblotting. FIG. 6 shows the immunoblotting results. PGRN levels doubled compared to DMSO at the highest concentrations (N=4). FIG. 7 shows the intensity of the bands in graphical form to show the increase in intensity.

Progranulin MEF cells were treated with one aliquot each of C15 and C19 and levels of lysotracker were analyzed to look for reduction of lysosome levels back to wild type levels. C19 showed a marked decrease in lysosome levels after one trial as shown in FIGS. 8A-8F.

All of the methods and apparatuses disclosed and claimed herein can be made and executed without undue experimentation in light of the present disclosure. While the compositions and methods of this disclosure have been described in terms of preferred embodiments, it will be apparent to those of skill in the art that variations may be applied to the methods and apparatuses and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Ahmed et al., *J. Neuroinflammation*, 4, 7, 2007.
Anderson et al., *BMC. Dev. Biol.*, 9:65, 2009.

Aramata et al., *Biochim. Biophys. Acta,* 1730:41-46, 2005.
Baker et al., *Nature,* 442, 916-919, 206.
Benkhelifa, et al., *Mol. Cell Biol.,* 21:4441-4452, 2001.
Bieliauskas and Pflum, *Chem. Soc. Rev.,* 37:1402-1413, 2008.
Borowiak and Melton, *Curr. Opin. Cell Biol.,* 21:727-732, 2009.
Brun and Gauthier, *J. Mol. Endocrinol.,* 40:37-45, 2008.
Buitrago et al., *Diabetologia,* 11:535-540, 1975.
Bundgaard, *Drugs of the Future,* 16:443-458, 1991.
Bundgaard, In: *Design of Prodrugs,* 7-9; 21-24, Elsevier, Amsterdam, 1985.
Capell et al., *J. Neurosci.,* 31, 1885-1894, 2011.
Chae et al., *Mol. Cells,* 18:271-288, 2004.
Chen et al., *J. Biol. Chem.,* 282:27215-27228, 2007.
Chen et al., *Nat. Chem Biol.,* 5:258-265, 2009.
Cruts et al., *Nature,* 442, 920-924, 206.
D'Amour et al., *Nat. Biotechnol.,* 24:1392-1401, 2006.
Doyle and Sussel, *Diabetes,* 56:1999-2007, 2007.
Eeckhoute et al., *Mol. Endocrinol.,* 15:1200-1210, 2001.
Eriksen and Mackenzie, *J. Neurochem,* 104, 287-297, 2008.
Fernandez-Zapico et al., *J. Biol. Chem.,* 284:36482-36490, 2009.
Finch et al., *Brain,* 132, 583-591, 2009.
Foulds et al., *Mol. Cell Biol.,* 24:10954-10964, 2004.
Gao et al., *Cell Metab.,* 6:267-279, 2007.
Gasa et al., *Differentiation,* 76:381-391, 2008.
Gasa et al., *Proc. Natl. Acad. Sci. USA,* 101:13245-13250, 2004.
Gass et al., *Hum. Mol. Genet.,* 15,2988-3001, 206.
Genuth et al., *Diabetes Care,* 26:3160-3167, 2003.
Goodge and Hutton, *Cell Dev. Biol.,* 11:235-242, 2000.
Greene and Wuts, In: *Protecting Groups in Organic Synthesis,* 3$^{rd}$ ed., John Wiley & Sons, Inc., 1999.
Gu et al., *Cell Metab.,* 11:298-310, 2010.
Gupta et al., *J. Clin. Invest.,* 115:1006-1015, 2005.
Habener and Stoffers, *Proc. Assoc. Am. Physicians,* 110:12-21, 1998.
Halban et al., *J. Clin. Endocrinol. Metab.,* 95:1034-1043, 2010.
Han et al., *Mol. Cell Biol.,* 27:6593-6605, 2007.
*Handbook of Pharmaceutical Salts: Properties, Selection and Use,* Stahl and Wermuth (Eds.), Verlag Helvetica Chimica Acta, 2002.
Hodges et al., *Neurology,* 61, 349-354, 2003.
Hollande et al., *J. Physiol. (Paris),* 72:815-832, 1976.
Huang et al., *Mol. Cell Biol.,* 20:3292-3307, 2000.
Kageyama et al., *Int. J. Biochem. Cell Biol.,* 29:1389-1399, 1997.
Kawakami et al., *Biomed. Pharmacother.,* 64:226-231, 2010.
Khoo et al., *J. Biol. Chem.,* 278:32969-32977, 2003.
Kim et al., *Cell,* 155(3):552-566, 2013.
Kirshner, *Curr. Neurol. Neurosci Rep,* 10, 504-511, 2010.
Kobinger et al., *Mol. Ther.,* 11:105-111, 2005.
Kroon et al., *Nat. Biotechnol.,* 26:443-452, 2008.
Lantz et al., *J. Clin. Invest.,* 114:512-520, 2004.
Lawrence et al., *J. Biol. Chem.,* 280:26751-26759, 2005.
Lawrence et al., *Proc. Natl. Acad. Sci. USA,* 105:13315-13320, 2008.
Lee et al., *Diabetes,* 51:2546-2551, 2002.
Lynn et al., *Proc. Natl. Acad. Sci. USA,* 104:10500-10505, 2007.
Lyttle et al., *Diabetologia,* 51:1169-1180, 2008.
Miyatsuka et al., *Proc. Natl. Acad. Sci. USA,* 108:185-190, 2011.
Muoio and Newgard, *Nat. Rev. Mol. Cell Biol.,* 9:193-205, 2008.
Neve et al., *Proc. Natl. Acad. Sci. USA,* 102:4807-4812, 2005.
Newgard and McGarry, *Annu. Rev. Biochem.,* 64:689-719, 1995.
Ohneda et al., *Semin. Cell Dev. Biol.,* 11:227-233, 2000.
Oliver-Krasinski and Stoffers, *Genes Dev.,* 22:1998-2021, 2008.
Qiu et al., *J. Biol. Chem.,* 279:9796-9802, 2004.
Qiu et al., *Mol. Cell Biol.,* 18:2957-2964, 1998.
Raum et al., *Mol. Cell Biol.,* 26:5735-5743, 2006.
Redmon et al., *Diabetes,* 43:546-551, 1994.
Russell et al., *ACS Chem Biol.* 7(6):1077-83, 2012.
Rutter and Parton, *Front Horm. Res.,* 36:118-134, 2008.
Sadek et al., *Proc. Natl. Acad. Sci. USA,* 105:6063-6068, 2008.
Sander et al., *Development,* 127:5533-5540, 2000.
Scearce et al., *Diabetes,* 51:1997-2004, 2002.
Schneider et al., *Nat. Chem. Biol.,* 4:408-410, 2008.
Schneider et al., *ACS Chem Neurosci.* 3(7):557-68, 2012.
Schwitzgebel et al., *Development,* 127:3533-3542, 2000.
Sharma et al., *Mol. Cell Biol.,* 19:704-713, 1999.
Sleegers et al., *Ann. Neurol.,* 65, 603-609, 2009.
Smith et al., J. *Biol. Chem.,* 275:36910-36919, 2000.
Smith et al., J. *Biol. Chem.,* 278:38254-38259, 2003.
Sommer et al., *Mol. Cell Neurosci.,* 8:221-241, 1996.
Steiner et al., *Diabetes Obes. Metab.,* 11(Suppl 4):189-196, 2009.
Steiner et al., *Islets.,* 2:135-145, 2010.
Tang et al., *Science, in press,* 2011.
Van Swieten and Heutink, *Lancet Neurol,* 7, 965-974, 2008
Vaxillaire and Froguel, *Endocr. Rev.,* 29:254-264, 2008.
Wang et al., *Diabetologia,* 50:348-358, 2007.
Wang et al., *J. Biol. Chem.,* 277:17564-17570, 2002.
Wang et al., *Proc. Natl. Acad. Sci. USA,* 106:1427-1432, 2009.
White et al., *Diabetes,* 57:654-668, 2008.
Wicksteed et al., *Cell Metab.,* 5:221-227, 2007.
Wilson et al., *Mech. Dev.,* 120:65-80, 2003.
Xu et al., *J. Biol. Chem.,* 273:4485-4491, 1998.
Zhang et al., *Cell Res.,* 19:429-438, 2009.
Zhou et al., *Nature,* 455:627-632, 2008.

What is claimed is:

1. A method of treating a subject having or suspect of having frontotemporal dementia comprising administering to said subject an effective amount of a 3',5'-disubstituted isoxazole having the formula:

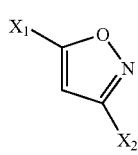

(I)

wherein:

$X_1$ is alkyl$_{(C \leq 12)}$ or heteroaryl$_{(C \leq 12)}$, or a substituted version of any of these groups;

or $X_1$ is

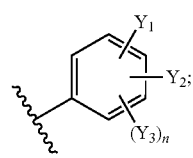

wherein:

$Y_1$ and $Y_2$ are each independently selected from hydrogen, halo, hydroxy, amino, nitro, or cyano, or alkyl$_{(C \leq 12)}$, alkoxy$_{(C \leq 12)}$, alkylamino$_{(C \leq 12)}$, dialkylamino$_{(C \leq 12)}$, or $Y_1$ and $Y_2$ are taken together to form

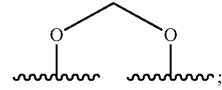

$Y_3$ is hydrogen, halo, hydroxy, amino, aminosulfonyl, nitro, cyano, mercapto, or phosphate;

alkyl$_{(C \leq 12)}$, alkenyl$_{(C \leq 12)}$, alkynyl$_{(C \leq 12)}$, aryl$_{(C \leq 12)}$, heteroaryl$_{(C \leq 12)}$, aralkyl$_{(C \leq 12)}$, acyl$_{(C \leq 12)}$, alkyloxy$_{(C \leq 12)}$, alkenyloxy$_{(C \leq 12)}$, alkynyloxy$_{(C \leq 12)}$, aryloxy$_{(C \leq 12)}$, heteroaryloxy$_{(C \leq 12)}$, aralkyloxy$_{(C \leq 12)}$, acyloxy$_{(C \leq 12)}$, alkylamino$_{(C \leq 12)}$, dialkylamino$_{(C \leq 12)}$, alkenylamino$_{(C \leq 12)}$, alkynylamino$_{(C \leq 12)}$, arylamino$_{(C \leq 12)}$, heteroarylamino$_{(C \leq 12)}$, aralkylamino$_{(C \leq 12)}$, amido$_{(C \leq 12)}$, alkylsulfonylamino$_{(C \leq 12)}$, alkylsulfonyl$_{(C \leq 12)}$, arylsulfonyl$_{(C \leq 12)}$, or a substituted version of these groups; and n is 1, 2, or 3; and $X_2$ is aryl$_{(C \leq 12)}$, substituted aryl$_{(C \leq 12)}$, or —C(O)NR$_1$R$_2$;

wherein:
R$_1$ and R$_2$ are independently selected from hydrogen, alkyl$_{(C\leq12)}$, substituted alkyl$_{(C\leq12)}$, alkenyl$_{(C\leq12)}$, substituted alkenyl$_{(C\leq12)}$, alkynyl$_{(C\leq12)}$, substituted alkynyl$_{(C\leq12)}$, aryl$_{(C\leq12)}$, substituted aryl$_{(C\leq12)}$, heteroaryl$_{(C\leq12)}$, substituted heteroaryl$_{(C\leq12)}$, aralkyl$_{(C\leq12)}$, substituted aralkyl$_{(C\leq12)}$, heteroaralkyl$_{(C\leq12)}$, substituted heteroaralkyl$_{(C\leq12)}$, or -A-Y$_4$ wherein A is alkanediyl$_{(C\leq12)}$ or substituted alkanediyl$_{(C\leq12)}$ and Y$_4$ is

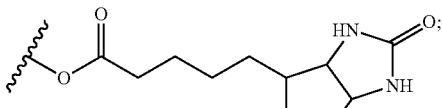

or when R$_1$ and R$_2$ are taken together, R$_1$ and R$_2$ are alkanediyl$_{(C\leq12)}$, alkoxydiyl$_{(C\leq12)}$, alkylaminodiyl$_{(C\leq12)}$, or a substituted version of any of these groups;
or a pharmaceutically acceptable salt thereof.

2. The method of claim 1, wherein said isoxazole is further defined by the formula:

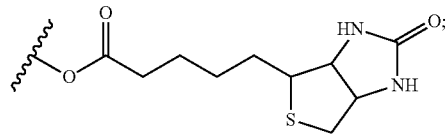

wherein:
X$_1$ is heteroaryl$_{(C\leq12)}$ or substituted heteroaryl$_{(C\leq12)}$; and
R$_1$ and R$_2$ are independently selected from hydrogen, alkyl$_{(C\leq12)}$, substituted alkyl$_{(C\leq12)}$, alkenyl$_{(C\leq12)}$, heteroaralkyl$_{(C\leq12)}$, or -A-Y$_4$ wherein A is alkanediyl$_{(C\leq12)}$ or substituted alkanediyl$_{(C\leq12)}$ and Y$_4$ is

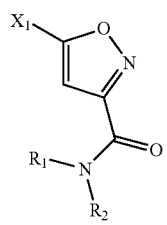

or when R$_1$ and R$_2$ are taken together, R$_1$ and R$_2$ are alkanediyl$_{(C\leq12)}$, alkoxydiyl$_{(C\leq12)}$, alkylaminodiyl$_{(C\leq12)}$, or a substituted version of any of these groups;
or a pharmaceutically acceptable salt thereof.

3. The method of claim 1, wherein the isoxazole has X$_1$ selected from 2-thienyl or 3-thienyl.

4. The method of claim 1, wherein the isoxazole has X$_2$ of —C(O)NR$_1$R$_2$.

5. The method of claim 1, wherein the isoxazole has R$_1$ and R$_2$ selected from alkyl$_{(C\leq12)}$ or substituted alkyl$_{(C\leq12)}$.

6. The method of claim 1, wherein the isoxazole has R$_1$ and R$_2$ selected from —CH$_2$CH$_2$CH$_2$CH$_3$, —CH$_2$(CH$_2$)$_4$CH$_2$OH, —CH$_2$CH$_2$CH$_3$, —CH$_2$(CH$_2$)3CH$_2$OH, cyclobutyl, or cyclopentyl.

7. The method of claim 1, wherein the isoxazole has R$_1$ and R$_2$ selected from alkenyl$_{(C\leq12)}$ or heteroaralkyl$_{(C\leq12)}$.

8. The method of claim 1, wherein the isoxazole has R$_1$ and R$_2$ of —CH$_2$CHCH$_2$.

9. The method of claim 1, wherein the isoxazole has R$_1$ and R$_2$ are taken together as alkanediyl$_{(C\leq12)}$, alkoxydiyl$_{(C\leq12)}$, or a substituted version of either of these groups.

10. The method of claim 1, wherein the isoxazole is further defined as a formula selected from:

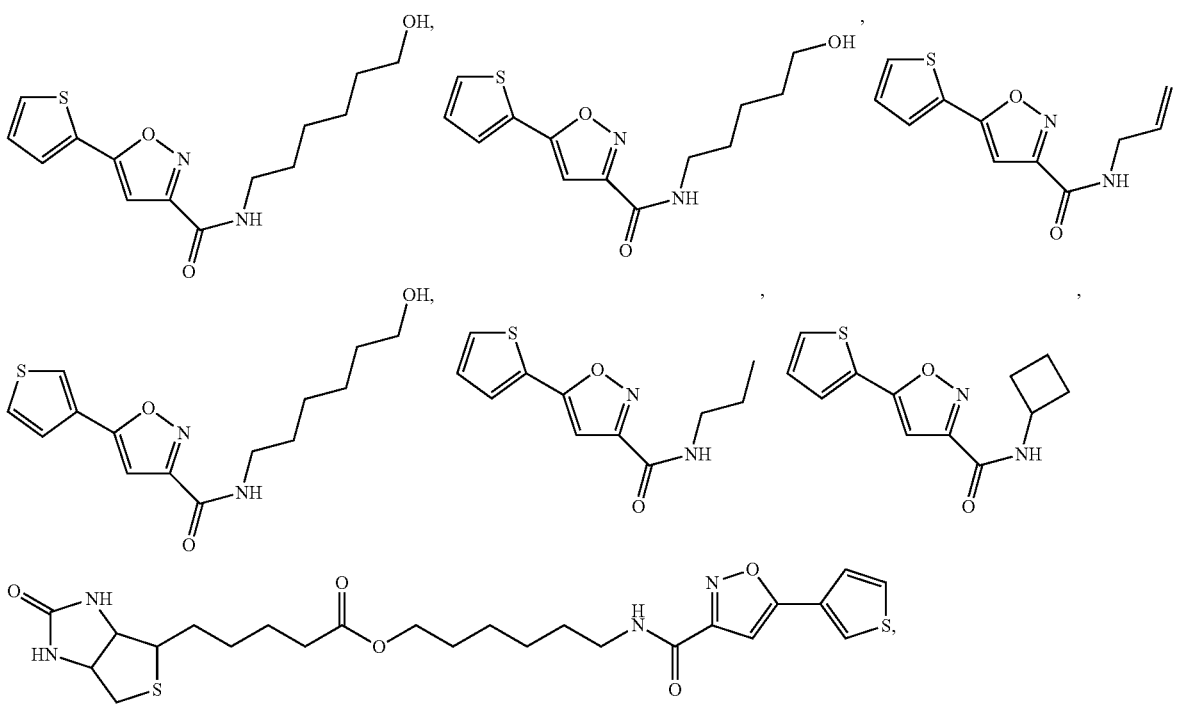

-continued

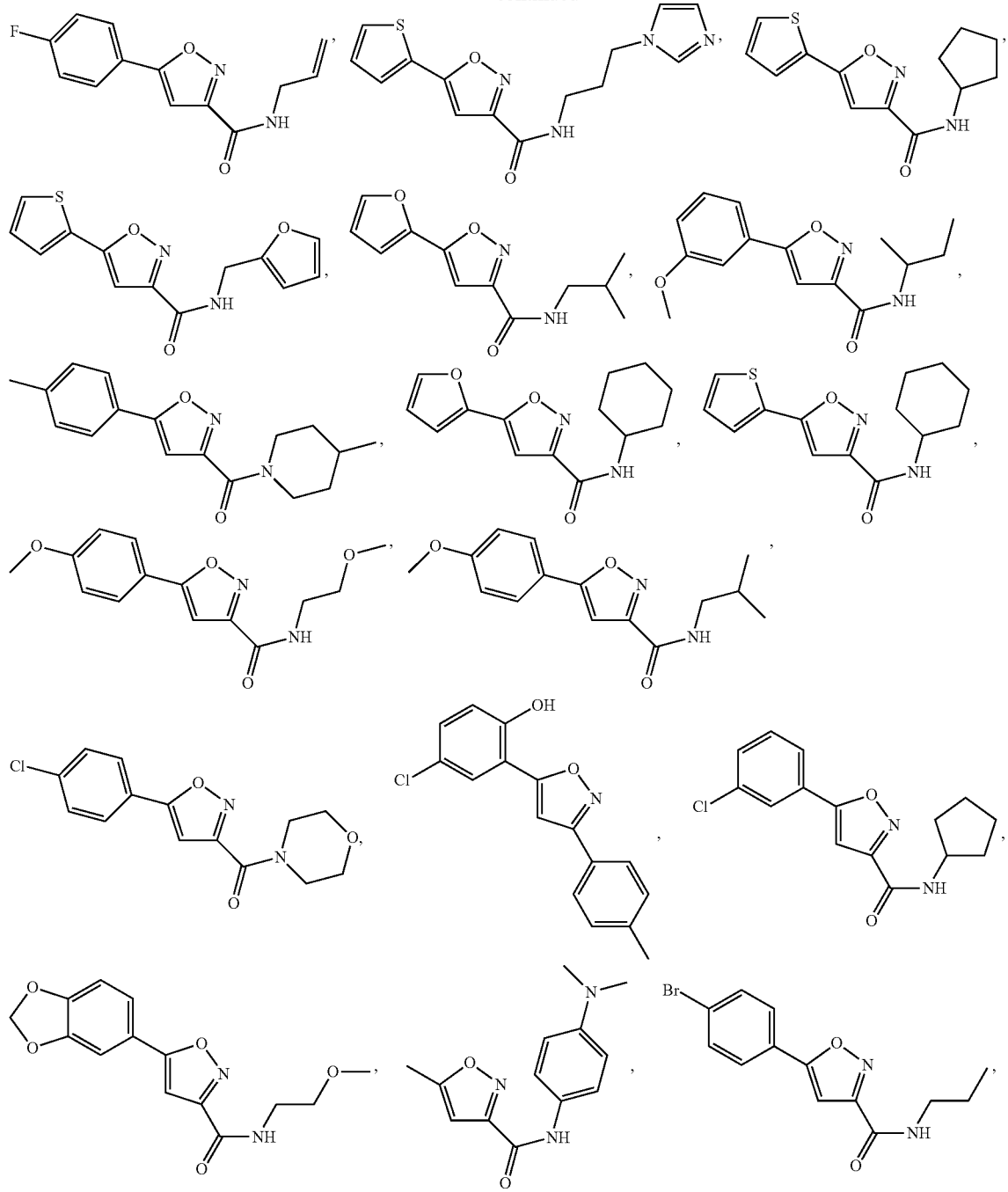

or a pharmaceutically acceptable salt thereof.

11. The method of claim 1, wherein administering comprises intravenous, intra-arterial, subcutaneous or oral administration.

12. The method of claim 1, wherein said subject is suspected of having frontotemporal dementia.

13. The method of claim 1, wherein said subject has been diagnosed as having frontotempral dementia.

14. The method of claim 13, wherein diagnosis is by identification of a loss-of-function function mutation in said subject's progranulin gene.

15. The method of claim 1, wherein administering comprises daily administration, every other day administration, weekly administration or monthly administration.

16. The method of claim 1, further comprising administering to said subject a second treatment.

17. The method of claim 16, wherein said second treatment comprises administration of a selective serotonin reuptake inhibitor.

18. The method of claim 1, wherein said subject exhibits Tau, TDP-43, or FUS pathology.

* * * * *

UNITED STATES PATENT AND TRADEMARK OFFICE
CERTIFICATE OF CORRECTION

PATENT NO. : 10,149,836 B2
APPLICATION NO. : 15/127603
DATED : December 11, 2018
INVENTOR(S) : Joachim Herz et al.

Page 1 of 1

It is certified that error appears in the above-identified patent and that said Letters Patent is hereby corrected as shown below:

In Claim 6, Column 40, Line 28, delete "–$CH_2(CH_2)3CH_2OH$" and insert -- –$CH_2(CH_2)_3CH_2OH$-- therefor.

Signed and Sealed this
Twenty-sixth Day of March, 2019

Andrei Iancu
*Director of the United States Patent and Trademark Office*

SEQUENCE LISTING

<160> NUMBER OF SEQ ID NOS: 11

<210> SEQ ID NO 1
<211> LENGTH: 19
<212> TYPE: PRT
<213> ORGANISM: Artificial sequence
<220> FEATURE:
<223> OTHER INFORMATION: Synthetic peptide

<400> SEQUENCE: 1

Val Pro Trp Met Lys Lys Val Ile Ala Pro Leu Arg Leu Pro Asp Pro
1               5                   10                  15

Gln Ile Leu

<210> SEQ ID NO 2
<211> LENGTH: 18
<212> TYPE: DNA
<213> ORGANISM: Artificial sequence
<220> FEATURE:
<223> OTHER INFORMATION: Synthetic primer

<400> SEQUENCE: 2
cgagggcacc tggaaaac                                              18

<210> SEQ ID NO 3
<211> LENGTH: 19
<212> TYPE: DNA
<213> ORGANISM: Artificial sequence
<220> FEATURE:
<223> OTHER INFORMATION: Synthetic primer

<400> SEQUENCE: 3
cacattcccc cggatatga                                             19

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
cagggacttc cagttgctgc                                            20

<210> SEQ ID NO 5
<211> LENGTH: 19
<212> TYPE: DNA
<213> ORGANISM: Artificial sequence
<220> FEATURE:
<223> OTHER INFORMATION: Synthetic primer

<400> SEQUENCE: 5
gcagcagtga tggccatcc                                             19

<210> SEQ ID NO 6
<211> LENGTH: 19
<212> TYPE: DNA
<213> ORGANISM: Artificial sequence
<220> FEATURE:
<223> OTHER INFORMATION: Synthetic primer

<400> SEQUENCE: 6
ggagatggca caggaggaa                                             19

<210> SEQ ID NO 7
<211> LENGTH: 19
<212> TYPE: DNA
<213> ORGANISM: Artificial sequence
<220> FEATURE:
<223> OTHER INFORMATION: Synthetic primer

<400> SEQUENCE: 7
gcccgtagtg cttcagctt                                             19

```
<210> SEQ ID NO 8
<211> LENGTH: 24
<212> TYPE: DNA
<213> ORGANISM: Artificial sequence
<220> FEATURE:
<223> OTHER INFORMATION: Synthetic primer

<400> SEQUENCE: 8
agttcgaatg tcctgactcc gcca                                        24

<210> SEQ ID NO 9
<211> LENGTH: 24
<212> TYPE: DNA
<213> ORGANISM: Artificial sequence
<220> FEATURE:
<223> OTHER INFORMATION: Synthetic primer

<400> SEQUENCE: 9
aagccactgc cctgttggtc cttt                                        24

<210> SEQ ID NO 10
<211> LENGTH: 21
<212> TYPE: DNA
<213> ORGANISM: Artificial sequence
<220> FEATURE:
<223> OTHER INFORMATION: Synthetic primer

<400> SEQUENCE: 10
ccggctactg tccagaggtc c                                           21

<210> SEQ ID NO 11
<211> LENGTH: 24
<212> TYPE: DNA
<213> ORGANISM: Artificial sequence
<220> FEATURE:
<223> OTHER INFORMATION: Synthetic primer

<400> SEQUENCE: 11 ctagggagt ttcaagaggc aggt                                         24
```